United States Patent [19]

Sell

[11] 4,082,955
[45] Apr. 4, 1978

[54] X-RAY APPARATUS

[75] Inventor: Leslie James Sell, Orangeville, Canada

[73] Assignee: Picker Corporation, Cleveland, Ohio

[21] Appl. No.: 603,264

[22] Filed: Aug. 11, 1975

[51] Int. Cl.² .............................................. G03B 41/16
[52] U.S. Cl. .................................. 250/445 T; 250/490
[58] Field of Search .................. 250/439, 444, 445 R, 250/445 T, 446, 447, 448, 449, 450, 523, 524, 525, 490

[56] References Cited

U.S. PATENT DOCUMENTS

| | | | |
|---|---|---|---|
| 3,708,664 | 1/1973 | Bock | 250/445 T |
| 3,838,286 | 9/1974 | Prendergast | 250/445 T |

Primary Examiner—Craig E. Church
Attorney, Agent, or Firm—Watts, Hoffmann, Fisher & Heinke Co.

[57] ABSTRACT

An X-ray apparatus which is readily convertible for conventional radiographic or tomographic operation includes an X-ray source and an imaging device movably supported on opposite sides of a patient support. For tomographic procedures, the source and the imaging device are interconnected by shielded drive system components to effect coordinated movement of the source and the device. For conventional radiography, the drive components are disconnected to permit independent movement of the source and the imaging device. The drive components are disconnected for conventional radiography by lowering the X-ray source and by operating a latch located near the imaging device. The drive components are connected for tomography by raising the X-ray source and by operating the latch. Other improvements such as the use of rotary encoders to provide a digital readout of the location of a tomographic examination plane and to control the operation of the source during tomographic procedures are described.

35 Claims, 18 Drawing Figures

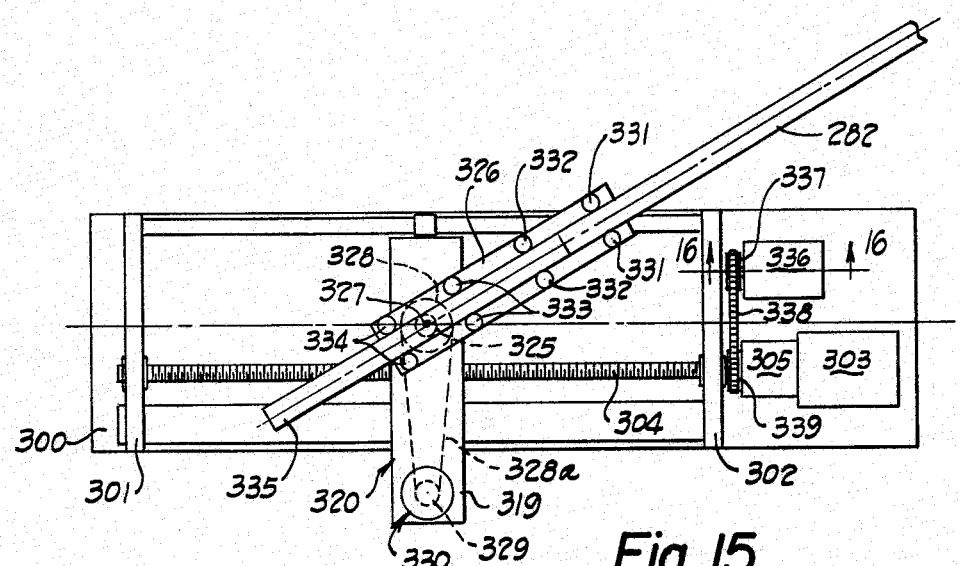
Fig. 15
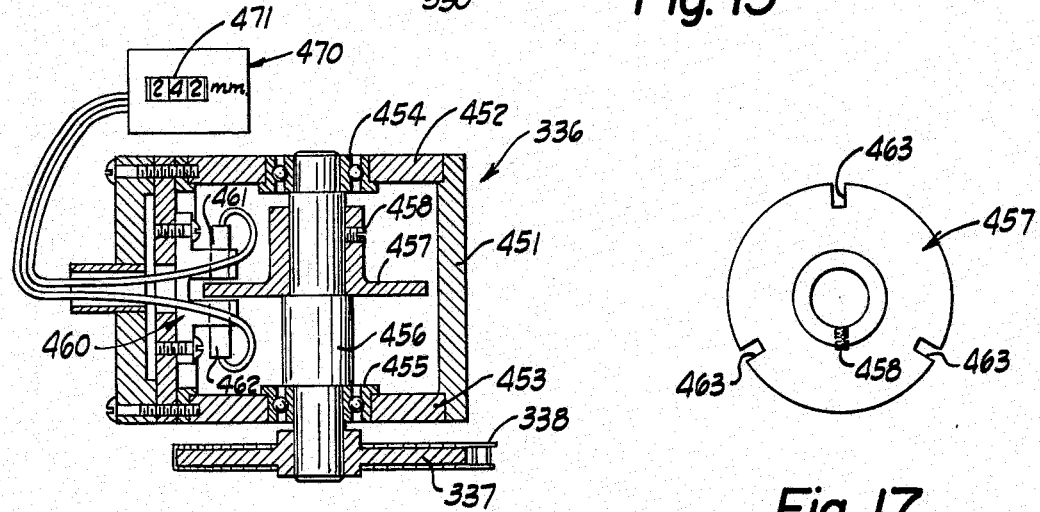
Fig. 16
Fig. 17
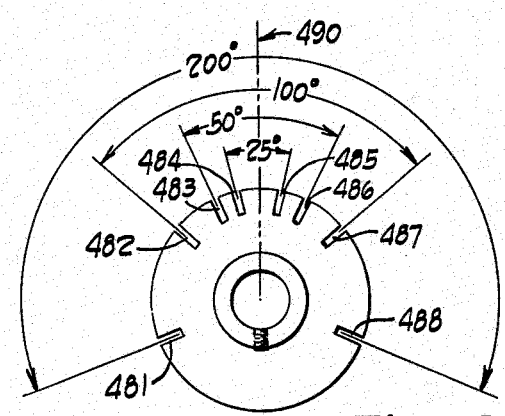
Fig. 18

X-RAY APPARATUS

BACKGROUND OF THE INVENTION

1. Field of the Invention

The present invention relates to X-ray apparatus and more particularly to novel and improved X-ray apparatus which is readily convertible for operation in conventional radiographic and tomographic modes.

2. Prior Art

In many conventional radiographic studies, a patient lies on the surface of an X-ray table and an X-ray source located above the table body is energized to direct controlled X-ray emission through a selected portion of the patient. X-radiation which has passed through the patient is incident on a film sheet carried in a Bucky or other film tray beneath the table top. The incident radiation exposes the film sheet to form a shadow image of a portion of the patient's anatomy.

In other conventional radiographic studies, the X-ray source is directed substantially horizontally toward a wall mounted film holder. A patient is positioned with his chest or other body portion adjacent the film holder and the source is energized to form a shadow image on a film sheet carried in the holder.

In another diagnostic procedure called tomography, a patient usually lies on the surface of the X-ray table while the X-ray source and the Bucky tray move in opposite directions in spaced paths longitudinal of the table top. During this movement, the source and the Bucky tray essentially pivot as a unit about an imaginary axis extending through an "examination plane" within the patient. The source is rotated during this movement to assure that it remains directed toward the Bucky. The movement causes images from above and below the examination plane to be blurred on the exposed film sheet, leaving as the only discernable information on the film, information from the examination plane.

In a multipurpose X-ray room, the X-ray apparatus must have exceptional flexibility if it is to meet the demands of these varied procedures. In view of the substantial costs involved in equipping and operating an X-ray room it is important that the installation be operated as efficiently as possible with minimum time being devoted to converting the apparatus for use from one type of procedure to another. The set-up time required to convert prior X-ray apparatus from conventional radiographic to tomographic use and vice versa has been unduly lengthy. Moreover, the set-up procedures have been unduly cumbersome and subject to error.

Typical prior apparatus includes a drive bar which interconnects the X-ray source and a film tray to coordinate their movement during tomography. The drive bar is movably supported on a pivot structure located between the source and the film tray. Since the source and the film tray must be movable independently for conventional radiographic procedures, a means of disconnecting the drive bar from one or both of the source and the film tray is provided.

In order to accommodate the increases and decreases in spacing between the source and the film tray which occur when the source and film tray are moved in parallel but opposite directions, the drive bar is provided with extensible ends. Connecting the drive bar ends with the source and film tray during conversion from conventional radiographic to tomographic operating modes necessitates that the extensible drive bar be physically aligned with and connected to other drive components which connect with the source and the film tray. This procedure is frequently cumbersome and time-consuming to effect, and requires a certain degree of strength, patience and coordination.

With some prior X-ray apparatus, the drive bar assembly is physically removed and stored during conventional radiography, and must be repositioned and mechanically interconnected with other drive system components for tomography. This procedure is likewise cumbersome, time-consuming, and subject to error if the drive bar assembly is improperly reconnected.

A further drawback of prior X-ray apparatus is that the drive bar and certain interconnecting linkage are exposed and extend in plain view during operation of the apparatus. The exposure of such components is necessitated both to facilitate access for connection and disconnection of the components, and because if guards were provided encompassing the wide arcs through which the components move, they would be excessive in size and would greatly inhibit freedom of access to a patient positioned on the table top. The exposed operating components are unsightly and pose safety concerns. The drive bar and its interconnecting components are typically located in relatively close proximity to one side of the table top and are found to inhibit ready access to a patient positioned on the table.

Exposed tomographic drive system components additionally present a sanitation problem. X-radiation opaque substances such as barium are frequently administered to a patient's digestive tract during radiography to facilitate diagnosis. Effluents from patients undergoing these procedures may discharge onto the apparatus and in that event must, of course, be cleaned up between procedures. The cleaning of exposed, complex drive system components is time-consuming and difficult.

Operating noise is a practical problem with some prior tomographic apparatus. The drive bar linkages provided on some prior tomographic apparatus together with other components which interconnect and guide the movements of the source and the Bucky tray tend to generate a substantial amount of noise as a tomograph is being produced. The exposed nature of these drive components facilitates the transmission of such noise into the surrounding environment. The sterile, accoustically reflective surfaces commonly found in X-ray rooms do little to attenuate such noise.

Prior tomographic drive systems have included a spaced array of mechanically actuated electrical switching components which are operative as the source and the film tray move during tomography to energize the source within a desired angular range of operation. A problem with this type of source control has been its complexity. Separate pairs of electrical switches have typically been required to define each desired angular range of source operation. If a prior apparatus is provided with a capability for operating the source selectively in 5°, 10°, 20°, and 40° ranges of operation, at least eight switches have been provided at spaced locations to control source operation in these ranges.

A further difficulty with many prior apparatus proposals has been their failure to provide a readily discernable and accurate readout of the location of the tomographic examination plane above the table top. Such mechanical indicators, as have been used on prior apparatus, have typically formed a part of the drive arm or its pivotal mounting structure and, as such, have been located behind the X-ray table along the upstanding tower.

SUMMARY OF THE INVENTION

The present invention overcomes the foregoing and other drawbacks of prior X-ray apparatus by providing a novel and improved X-ray apparatus which is readily convertible between conventional radiographic and tomographic operating modes.

An X-ray apparatus embodying the preferred practice of the invention includes a base and an elongated table top carried by the base. An upstanding tower is carried by the base for movement longitudinally of the table top. A carriage is supported on the tower for movement along the tower toward and away from the table top. An extensible arm is supported on the carriage and extends over the table top. An X-ray source is supported on the extensible arm. An X-ray imaging device is supported within the base for movement longitudinally of the table top.

A novel and improved drive system is provided to interconnect and drive the X-ray source and the imaging device through coordinated movements for tomography. The drive system includes components which are housed within and shielded by the extensible arm, by the tower, and by the base. A proportioning arm is carried within the base and forms one component of the drive system. The proportioning arm pivots about a vertical axis. The location of this axis is controlled by a carriage which is movable to determine the ratio of the relative movements executed by opposite ends of the proportioning arm as the arm pivots.

The proportioning arm is extensible and its opposite ends are constrained to move along parallel paths, longitudinally of the table top. One end of the proportioning arm is releasably connected to the imaging device. The other end is connected to the upstanding tower. As the tower is moved longitudinally of the table top in one direction during tomography, the proportioning arm is caused to pivot, and drives the imaging device a proportional distance in the opposite direction.

The drive components housed within the tower are connected to the proportioning arm and rotate in response to pivotal movement of the proportioning arm. The drive components carried within the extensible arm are connectable to the drive components carried in the tower when the carriage is positioned at a predetermined location along the tower, and rotate in response to pivotal movement of the proportioning arm. The arm-carried and the tower-carried drive components function to angulate the X-ray source during tomography to keep the X-ray beam emanating from the source aligned with the imaging device.

One important feature of the apparatus of the present invention is that the pivotally mounted exposed drive bar used on prior apparatus has been eliminated. The only drive components which extend vertically between the table base and the overhead extensible are carried in and shielded by a tubular supporting column. The proportioning function of prior drive bars is assumed by a proportioning arm which operates within the relatively large shielded space provided by the table pedestal.

All drive system components are in fact shielded from contact. The improved drive system not only eliminates the exposed drive bar used on prior apparatus to interconnect the coordinate the movement of the source and the imaging device, but also shields and guards its components enabling their operation with less noise, without detracting from the appearance of the apparatus and without posing safety concerns.

The tower-carried components occupy minimal space in the vicinity of the patient and permit ready access to a patient positioned on the table top. The shielded nature of the drive system components inhibits patient effluents from accumulating within the tomographic drive system, and facilitates clean-up procedures when required.

Conversion between conventional radiographic and tomographic modes of operation is effected simply by energizing two electrically operated devices, one of which moves the X-ray source along is supporting tower into or out of a predetermined "drive interconnect position" where the tower-carried and the arm-carried drive components drivingly connect, and the other of which latches or unlatches the imaging device to the drive system. In short, a simple, foolproof system is provided which substantially automatically converts the apparatus from readiness for radiographic work to readiness for tomographic work, and vice versa.

Separate electrically operated drive systems are provided for moving the tower along the table, for moving the carriage along the tower, for extending and retracting the extensible support arm, and for positioning the proportioning arm carriage to determine the location of the plane of tomographic examination. Separate sensors are provided to sense when the tower is centered along the table, where the carriage is positioned along the tower, the degree of extension of the support arm, whether arm-carried drive components are extended, and whether the Bucky tray is latched to the drive system.

The extensible arm can be rotated around the tower to perform certain radiographic procedures. A control lever is provided on the arm for releasing a latch and for retracting certain arm-carried drive components to permit rotation of the arm around the tower.

A pir of rotary encoders connect with the tomographic drive system. One provides a pulsed output signal which is interpreted by a digital display system to give an accurate digital reading in millimeters of the exact location of the examination plane. The other provides a pulsed output signal which is used to energize the X-ray source within one of several predetermined angular ranges of operation.

An object of the invention is to provide an X-ray apparatus which is readily operable in both radiographic and tomographic modes.

Another object is to provide a tomographic X-ray apparatus having a novel and improved drive system.

Other objects and a fuller understanding of the invention may be had by referring to the following description and claims taken in conjunction with the accompanying drawings.

BRIEF DESCRIPTION OF THE DRAWINGS

FIGS. 5 and 6 are sectional views as seen from planes indicated by lines 5—5 and 6—6 in FIG. 4;

FIG. 15 in an enlarged schematic top plan view of portions of the apparatus shown in FIGS. 1 and 14;

FIG. 16 is a sectional view of one of the rotary encoders shown in FIG. 15, as seen from a plane indicated by a line 16—16 in FIG. 15; and FIGS. 17 and 18 are top plan views of two discs used in separate ones of the rotary encoders shown in FIG. 15.

DESCRIPTION OF THE PREFERRED EMBODIMENT

Figure 1:
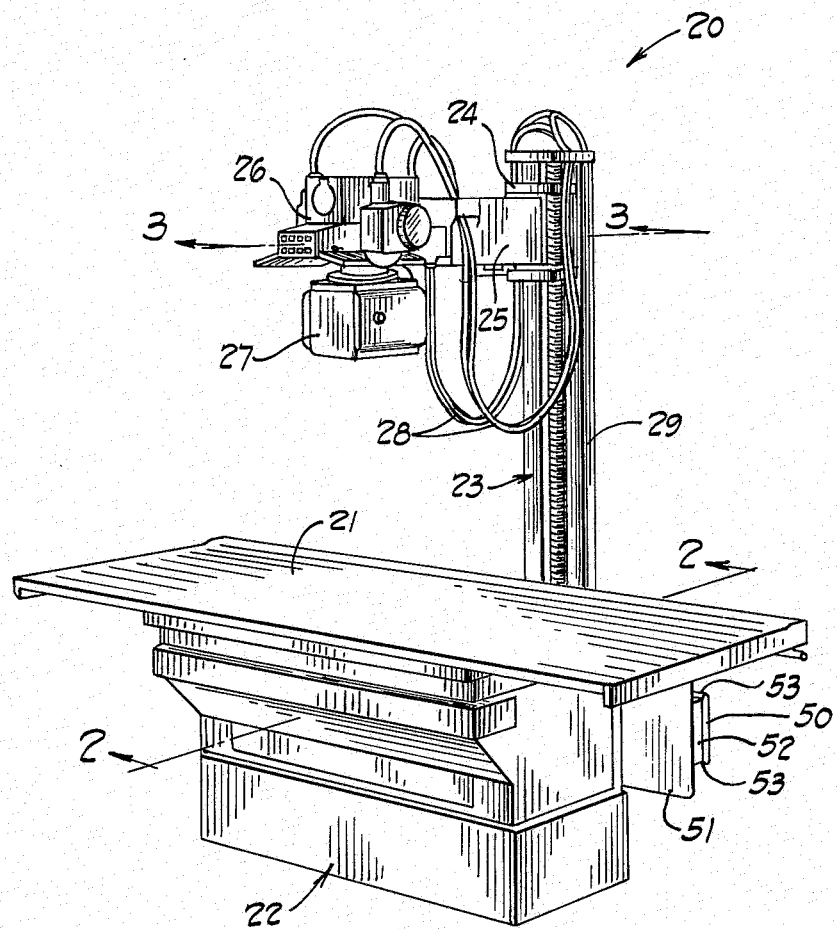
FIG. 1 is a perspective view of an X-ray apparatus constructed in accordance with the preferred practice of the present invention.

Referring to FIG. 1, an X-ray apparatus is indicated generally by the numeral 20. The apparatus 20 includes a table top 21 supported on a pedestal 22. A tower 23 is carried by the pedestal 22 for movement longitudinally of the table top 21. A carriage 24 is supported on the tower 23 for vertical movement along the tower 23. An extensible support arm 25 is connected to the carriage 24 and supports an X-ray source 26 including a collimator 27. Suitable power cables 28 extend up through a tubular conduit 29 at the rear of the tower 23 and connect with the X-ray source 26.

Figure 2:
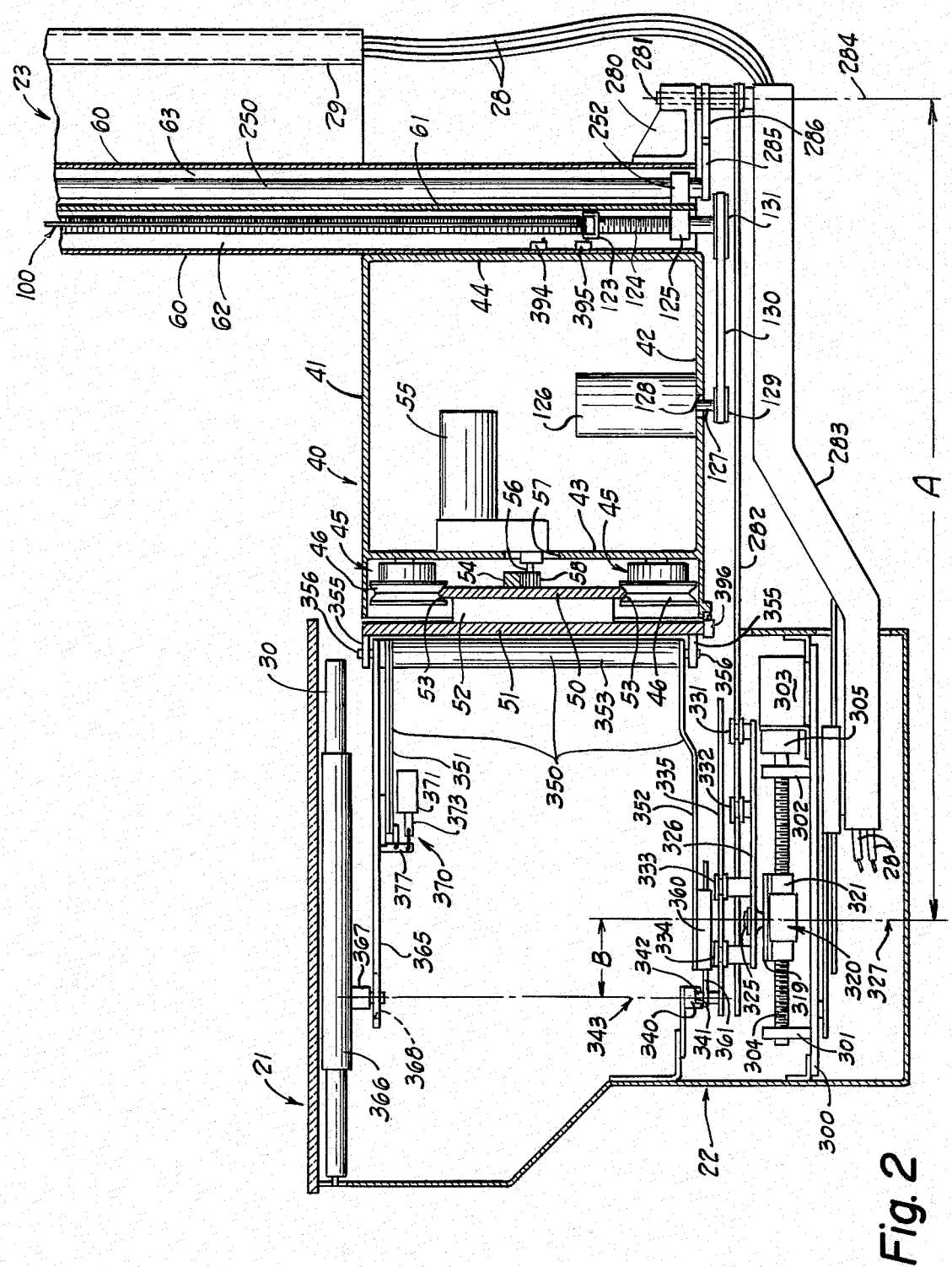
FIGS. 2 and 3 are enlarged sectional views as seen from planes indicated by lines 2—2 and 3—3 in FIG. 1.

Referring to FIG. 2, a film cassette holder 30 called a Bucky tray is supported beneath the table top 21. In operation, X-radiation emitted by the source 26 passes through portions of a patient positioned on the table top 21 and forms an image on a cassette-carried film sheet supported in the Bucky tray 30.

I. The Tower 23

The tower 23 is supported on a base carriage 40 for movement longitudinally of the table top 21. Referring to FIG. 2, the base carriage 40 is interposed between the pedestal 22 and the tower 23. The carriage 40 includes a framework having top and bottom walls, 41, 42, a front wall 43, and a rear wall 44. A plurality of rollers 45 are rotatably carried on the front wall 43. The rollers 45 have a V-shaped peripheral grooves 46.

A track 50 is carried by the pedestal 22. A mounting plate 51 forms part of the pedestal 22 and extends longitudinally beneath the table top 21, as shown in FIG. 1. A plurality of spacers 52 rigidly connect the mounting plate and the track 50.

The rollers 45 ride along opposite sides of the track 50. The top and bottom sides of the track are provided with V-shaped surfaces 53 which extend into the roller grooves 46. The interconnection between the rollers 45 and the track 50 mounts the base carriage 40 for movement longitudinally of the table top 21.

A toothed gear rack 54 is carried on the track 50 and extends longitudinally along the track 50. A reversible drive motor 55 is supported inside the base carriage 40 and has a drive shaft 56. The drive shaft 56 projects through a hole 57 formed in the front wall 43. A toothed gear 58 is secured to the drive shaft 56 and drivingly engages the gear rack 54. When the drive shaft 56 rotates in one direction, the base carriage 40 moves rightwardly along the track 50, as viewed in FIG. 1. When the motor 55 rotates the shaft 56 in the opposite direction, the base carriage moves leftwardly along the track 50.

Figure 3:
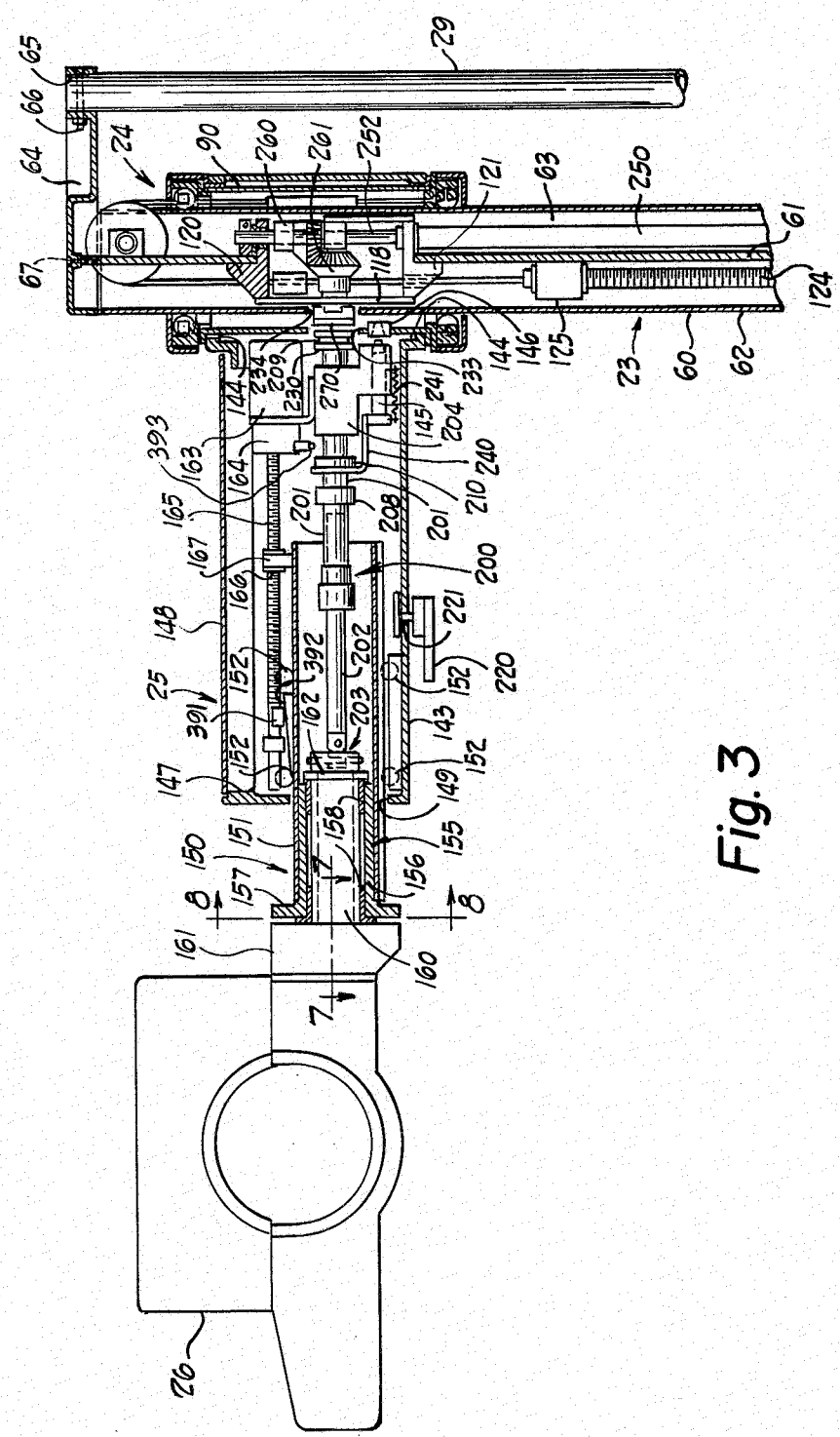

Referring to FIGS. 2 and 3, the tower 23 includes an upstanding tubular column 60 which is generally square in cross-section. The column 60 is secured to the rear wall 44 of the base carriage 40. A mounting plate 61 extends vertically within the column 60, dividing the column 60 into two elongated chambers 62, 63.

Figure 4:
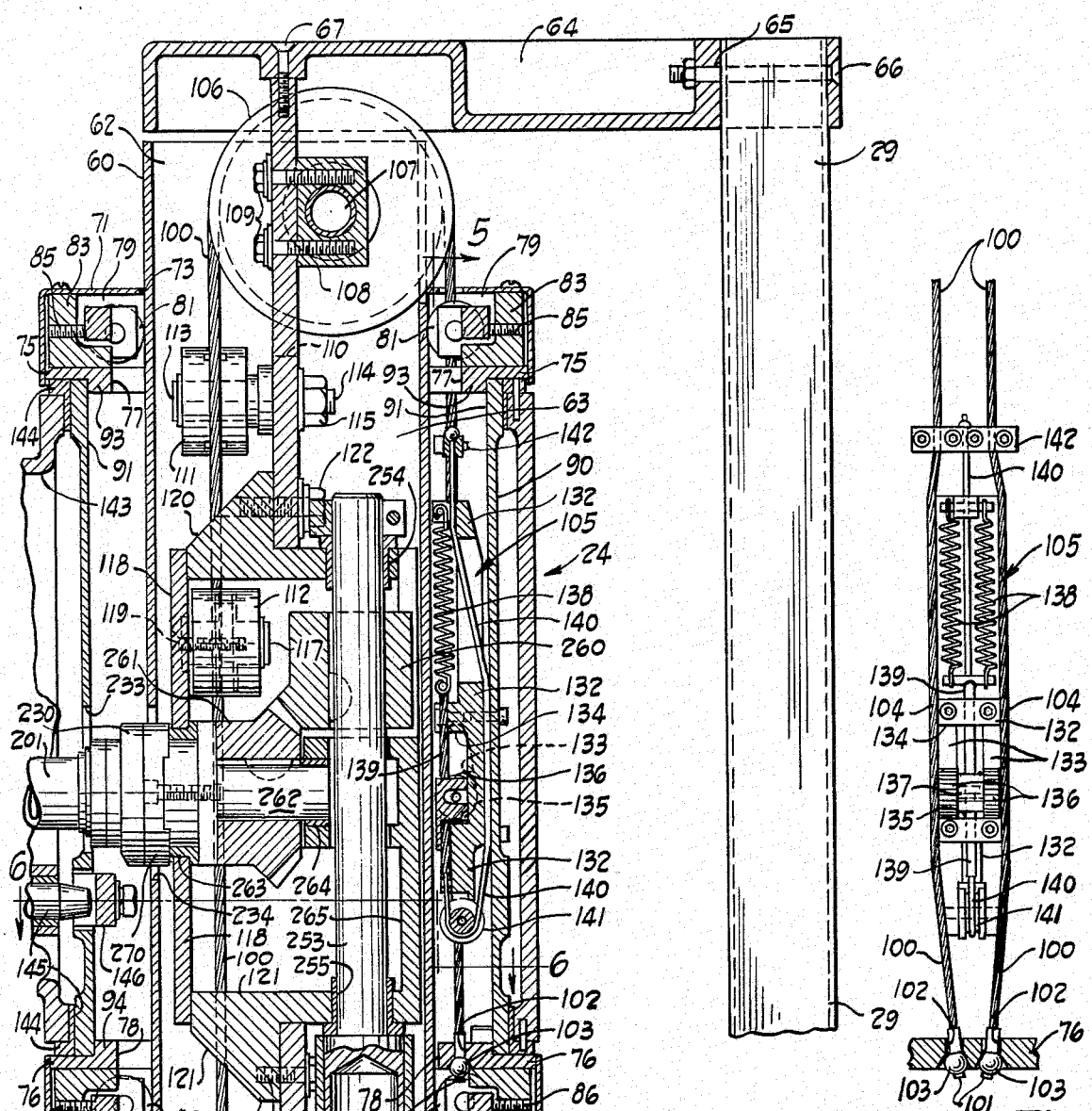
FIG. 4 is a sectional view showing a portion of FIG. 3 on an enlarged scale.

Referring to FIGS. 3 and 4 a cover 64 interconnects the upper end of the column 60 and the conduit 29. The conduit 29 is of rectangular cross-section and extends through a hole 65 formed in the cover 64. A threaded fastener 66 extends through alonged holes formed in the cover 64 and in the conduit 29 to secure the cover 64 to the conduit 29. Threaded fasteners 67 extend through holes formed in the cover 64 and are threaded into the mounting plate 61 to secure the cover 64 to the mounting plate 61.

II. The Carriage 24

The carriage 24 includes top and bottom covers 71, 72. Openings 73, 74 are formed through the covers 71, 72 to receive the column 60. Upper and lower support plates 75, 76 are positioned inside the covers 71, 72. Openings 77, 78 are formed through the plates 75, 76 to receive the column 60. The covers 71, 72 and the plates 75, 76 cooperate to define a pair of chambers 79, 80 that perimetrically surround the column 60.

Upper and lower sets of rollers 81, 82 are provided within the chambers 79, 80 to movably support the carriage 24 on the column 60. Upper and lower bracket assemblies 83, 84 rotatably support the rollers 81, 82. The bracket assemblies 83, 84 include set screws 85, 86 to position the rollers 81, 82 transversely of the column 60 so that the rollers 81, 82 will snugly engage the periphery of the column 60.

A cylindrical collar 90 interconnects the support plates 75, 76. The collar 90 has a longitudinally extending circular bore 91. The plates 75, 76 have annular flanges 93, 94 which extend into the ends of the bore 91. Threaded fasteners, now shown, secure the plates 75, 76 to the collar 90.

A cable and pulley system supports the carriage 24 for vertical movement along the tower 23. Referring to FIGS. 4 and 5, a pair of cables 100 have end regions 101 which extend through a pair of holes 102 formed in the lower support plate 76. A pair of cable end clamps 103 retain the cable end regions 101 in the holes 102.

The cables 100 have reaches 104 which extend upwardly alongside a carriage locking assembly 105, and are reeved around a pair of pulleys 106. A shaft 107 mounts the pulleys 106. Bearing blocks 108 journal opposite end portions of the shaft 107. Threaded fasteners 109 secure the bearing blocks 108 to the mounting plate 61. The pulleys 106 extend through an opening 110 formed in the mounting plate 63.

Two pairs of idler rollers 111, 112 are provided in the upper end of the chamber 62 to widen the distance between the cables 100 as they depend further into the chamber 62. The rollers 111 are relatively closely spaced rollers which receive the cables 100 as they depend from the pulleys 106. The rollers 112 are relatively widely spaced rollers which widen the distance between the cables 100 to that shown in FIG. 6.

A pair of stub shafts 113 journal the rollers 111. The stub shafts 113 have threaded end regions 114 which extend through holes formed in the mounting plate 61. Threaded fasteners 115 secure the stub shafts 113 in place on the mounting plate 61.

A pair of stub shafts 117 journal the rollers 112. The stub shafts 117 are secured to a plate 118 by threaded fasteners 119. A pair of brackets 120, 121 are secured to upper and lower end regions of the plate 118. Threaded fasteners 122 mount the brackets 120, 121 on the mounting plate 61.

Referring to FIG. 2, the cables 100 depend through the chamber 62 and have ends secured to a bracket 123. The bracket 123 is threaded to receive a threaded rod 124. A pair of bearing blocks 125 are secured to the mounting plate 61 and journal the rod 124 for rotation.

A reversible drive motor 126 is mounted within the base carriage 40 for raising and lowering the carriage 24 along the tower 23. The motor 126 has a drive shaft 127 which depends through an opening 128 formed in the bottom wall 42. A pulley 129 is mounted on the drive shaft 127. A drive belt 130 is reeved around the pulley 129 and around a pulley 131 secured to the threaded rod 124. When the motor 126 rotates the threaded rod 124 in one drive direction, the bracket 123 moves up the rod 124, causing the carriage 24 to move downwardly along the tower 23. When the motor 126 rotates the threaded rod 124 in the opposite drive direction, the bracket 123 moves down the rod 124, causing the carriage 24 to move upwardly along the tower 23.

The carriage locking assembly 105 is operable in the event of failure of the cables 100 to arrest downward movement of the carriage 24 along the column 23. Referring to FIGS. 4 and 5, the carriage locking assembly includes a bracket 132 mounted on the inner wall of the collar 90. A pair of surfaces 133 defining inclined trackways facing toward the column 60 are formed on the bracket 132. Upper and lower stop surfaces 134, 135 are provided at opposite ends of the trackway surfaces 133.

A pair of rollers 136 are positioned between the stops 134, 135 adjacent the trackways 133. A roller support bracket 137 rotatably carries the rollers 136.

A pair of tension coil springs 138 have their upper end regions connected to the upper end region of the bracket 132. A T-shaped member 139 connects with the lower end regions of the springs 140 and has a stem portion which depends through and is clamped by the roller support bracket 137. A flexible cable 140 conncts with the lower end region of the T-shaped member 139 and is reeved around a pulley 141 carried on the lower end region of the bracket 132. A reach of the cable 140 extends upwardly from the pulley 141 and is secured to a cable clamping bracket 142.

The cable clamping bracket 142 clamps the cables 100 at a position above the bracket 132, securing the cables 100, 140 together for concurrent movement. The cable clamping bracket 142 is positioned on the cables 100 at a location which will extend the tension coil springs 138 and which will position the rollers 136 near the lower stop surfaces 135.

If one or both of the cables 100 should fail, the clamping bracket 142 will no longer be held upwardly by the cables 100. The springs 138 will then be operative to move the rollers 136 rapidly upwardly along the trackways 133 and into wedging engagement with the outer surface of the column 60. The wedging engagement between the rollers 136 and the column 60 will arest downward movement of the carriage 24, thereby preventing the carriage 24, the extensible arm 25, and the X-ray source 26 from dropping any significant distance toward the table top 21.

III. The Extensible Arm 25

Referring to FIG. 3, the extensible support arm 25 includes a housing 143. The housing 143 is supported on the collar 90 for limited rotation around the column 60. A pair of annular bearing rings 144 are carried in top and bottom ends of the housing 143 to journal the collar 90.

A releasable lock is provided to facilitate the retention of the extensible arm 25 in an attitude extending forwardly of the tower 23. This lock remains engaged during tomographic procedures and during all radiographic procedures except when the arm 25 must be rotated around the column 60 to position the source 26 for a special radiographic procedure.

Figure 6:
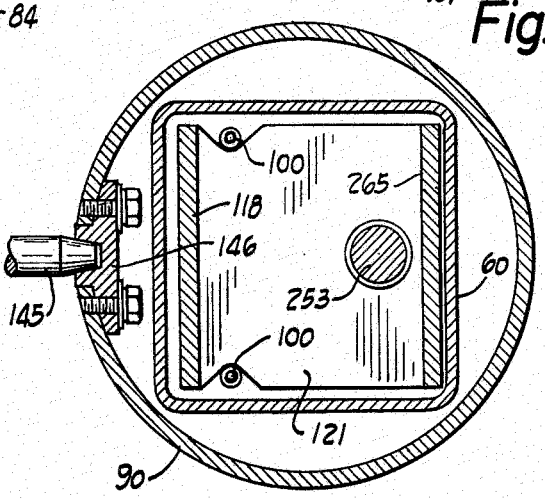

Referring to FIGS. 3, 4 and 6 the lock includes a locking pin 145 carried in the arm 25, and an apertured block 146 carried by the collar 90. When the locking pin 145 is latched in engagement with the locking block 146, as shown in FIGS. 4 and 6, the arm 25 cannot rotate around the column 60. When the locking pin 145 disengages the locking block 146, the arm 25 is rotatable about the collar 90. The mechanism which unlatches the locking pin 145 will be described later.

The housing 143 projects forwardly of the tower 23 to overlie the table top 21. An upwardly facing opening 147 is formed in the housing 143. A cover plate 148 closes the opening 147. A forwardly facing opening 149 is provided in the forward end of the housing 143.

An extensible arm section 150 is telescopically carried by the housing 143. The arm section 150 includes a tubular member 151 which extends through the opening 149. A plurality of rollers 152 are carried inside the housing 143. The rollers 152 engage the peripheral surface of the tubular member 151 to support the arm section 150 for telescopic movement relative to the housing 143.

A sleeve 155 is carried by the tubular member 151. The sleeve 155 has a tubular portion 156 which extends into the forward end of the tubular member 151, and a flange portion 157 located forwardly of the tubular member 151. A pair of bushings 158 are provided inside opposite end regions of the sleeve 155.

A hollow shaft 160 extends through the bushings 158. A mounting block 161 is connected on one end region of the shaft 160. The X-ray source 26 is supported on the mounting block 161. A collar 162 is carried near the opposite end region of the shaft 160. The mounting block 161 and the collar 162 engage outer ends of the bushings 158 and inhibit axial movement of the shaft 160 relative to the arm section 150.

A reversible drive motor 163 is supported within the housing 143. A ball bearing speed reducer 164 drivingly connects the motor 163 to a threaded rod 165. A nut 166 is threaded onto the rod 165. A bracket 167 mounts the nut 166 on the inner end region of the tubular member 151. When the motor 163 rotates the threaded rod 165 in one direction, the nut 166 moves leftwardly along the rod 165, as viewed in FIG. 3, causing the arm section 150 to extend leftwardly relative to the housing 143. When the motor 163 rotates the rod 165 in the opposite direction, the nut 166 moves rightwardly along the rod 165, drawing the arm section 150 inwardly of the housing 143.

IV. The X-ray Source 26

The X-ray source 26 is movable relative to the table top 21 in five independent ways:
1. Through movement of the tower 23 longitudinally of the table top 21, as has been described;
2. Through movement of the carriage 24 vertically along the tower 23, as has been described;
3. Through rotation of the arm 25 on the carriage 24 about the vertical axis of the column 60, as has been described;
4. Through extension and retraction of the extensible arm 25 laterally of the table top 21, as has been described; and
5. Through rotation about the axis of the hollow shaft 160, as will now be described.

The shaft 160 is journaled for rotation by the bushings 158. The X-ray source 26 is rotatable with the shaft 160 through an angle of 180° between horizontal attitudes. Two devices are operative to inhibit rotation of the X-ray source about the axis of the shaft 160. One of these devices is a friction brake 170. The other is a detent assembly 179.

Figure 7:
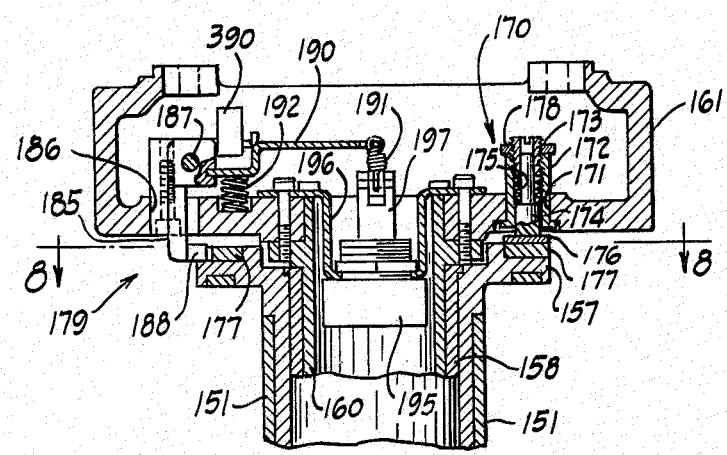
FIGS. 7 and 8 are sectional views as seen from planes indicated by lines 7—7 and 8—8 in FIG. 3.
Figure 8:
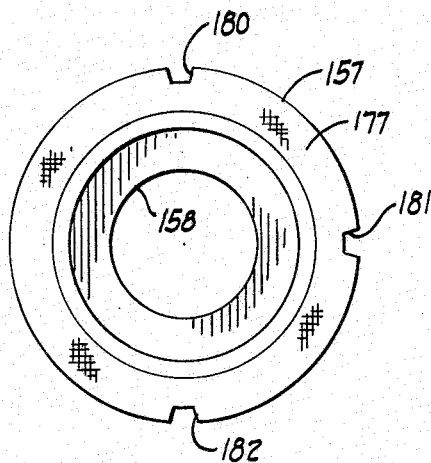

Referring to FIGS. 7 and 8, the friction brake 170 in an assembly which is interposed between the X-ray source 26 and the extensible arm 25 to hold the X-ray source 26 in a selected rotary orientation. An aperture 171 is provided in the mounting block 161 facing toward the flange 157. A tubular housing 172 is pressed into the aperture 171. A set screw 173 is threaded into one end region of the tubular housing 172. A plunger 174 is slidably carried in the other end region of the housing 171. A compression coil 175 spring is interposed between the set screw 173 and the plunger 174 and biases the plunger 174 toward the flange 157.

Friction brake material in the form of a braking pad 176 is carried on the plunger 174. The brake pad 176 is engagable with an annular ring 177 carried on the flange 157.

The drag force provided by the friction brake 170 as the plunger-carried braking pad 176 drags along the ring 177 is easily adjusted by threading the set screw 173 into or out of the tubular housing 172. The set screw 173 is adjusted to provide a drag force sufficient to hold the X-ray source 26 in a selected position, but which will still permit an operator to rotate the source 26 easily. Once the set screw 173 is properly adjusted, it is locked in place by tightening a locking nut 178 into engagement with one end of the housing 172.

Referring again to FIGS. 7 and 8, the detent assembly 179 facilitates positioning the X-ray source in vertical and horizontal attitudes. Three detent notches 180, 181, 182 are provided in the ring 177. The notches 180, 182 correspond to horizontal orientations of the X-ray source 26. The notch 181 is used for downward vertical orientation of the source 26.

Referring to FIG. 7, a detent lever 185 is provided for selectively engaging the notches 180, 181, 182. The lever 185 extends through a hole 186 formed in the mounting block 161. A pin 187 extends through one end region of the lever 185 and pivotally mounts the lever 185 for movement about the axis of the pin 187. A detent projection 188 is formed on the opposite end region of the lever 185 for engaging the notches 180, 181, 182.

An arm 190 has one end rigidly connected to the lever 185. A compression coil spring 192 is interposed between the arm 190 and the mounting block 161. The compression spring 192 biases the arm 190 and the lever 185 counterclockwise as viewed in FIG. 7 to urge the detent projection 188 in one of the notches 180, 181, 182.

An electrically operated solenoid 195 is provided to pivot the arm 190 and the lever 185 clockwise to move the projection 188 out of one of the notches 180, 181, 182. A bracket 196 supports the solenoid 195 inside the hollow shaft 160. The solenoid 195 has an armature 197 which is movable axially of the hollow shaft 160. A tension coil spring 191 interconnects one end of the arm 190 and the armature 197. When the solenoid 195 is electrically energized, the armature 197 moves axially inwardly of the hollow shaft 160, pivoting the arm 190 against the action of the compression spring 192 and releasing the detent projection 188 from one of the notches 180, 181, 182.

V. Driven Movement of the X-ray Source 26 and the Bucky Tray 30

If a tomograph is to be made with the X-ray apparatus 20, the X-ray source 26 and the Butky tray 30 are driven back and forth in opposite directions longitudinally of the table top 21. Simultaneously with such longitudinal movement, the source 26 is rotated about the axis of the hollow shaft 160 to keep the X-ray beam centered on a target area within a patient positioned on the table top 21.

Translation of the source 26 longitudinally of the table top 21 is effected by moving the tower 23 along the track 50. The reversible drive motor 55 (FIG. 2) is energized alternately in forward and reverse modes to effect this movement.

Rotation of the source 26 in coordination with its translation, and reciprocation of the Bucky tray 30 are effected by a drive system having interconnected components located in the table pedestal 22, in the tower 23, and in the extensible support arm 25.

A. The Arm-carried Drive Components

Referring to FIG. 3, a telescoping drive shaft 200 extends through the extensible arm 25. The shaft 200 includes a hollow tubular section 201 and a solid inner section 202. A universal joint 203 connects the inner shaft section 202 to the hollow shaft 160. A bearing block 204 is supported by the housing 143 and slidably journals the hollow section 201. A pair of spaced collars 208, 210 are mounted on the hollow shaft section 201.

The hollow shaft section 201 is movable axially relative to the bearing block 204. When the hollow shaft section 201 is positioned as shown in FIG. 3, it is in what will be called its "retracted" position. As will be explained, when the shaft section 201 is retracted, it is disconnected from a drive system carried in the column 60.

When the shaft section 201 is positioned such that the collar 210 abuts the bearing block 204, the shaft section is in what will be called its "extended" position. The shaft section 201 is normally kept in its extended position and is retracted only when it is necessary to rotate the extensible arm about the collar 90 for a special radiographic procedure. As will be explained, when the shaft section 201 is extended, it in no way hinders movement of the carriage 24 vertically along the tower 23.

Figure 10:
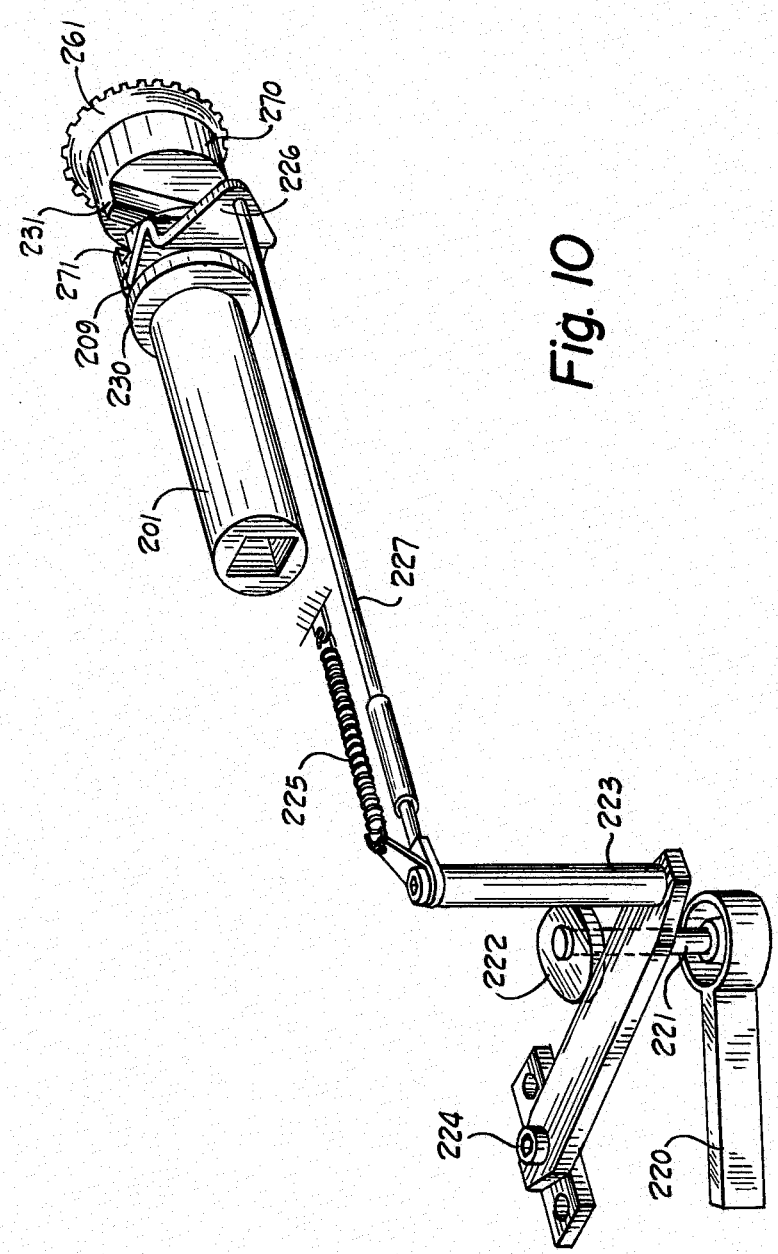
FIG. 10 is an enlarged perspective schematic view illustrating the relationship of several components of the structure shown in FIG. 3.

Movement of the shaft section 201 between its extended and retracted positions is effected by operating a lever 220. Referring to FIGS. 3 and 10, the lever 220 is located on the underside of the housing 143. A shaft 221 connects with the lever 220 and extends upwardly through an opening in the housing 143.

Referring to FIG. 10, a cam 222 is mounted on the upper end region of the shaft 221. An L-shaped arm 223 is pivoted at 224. A tension coil spring 225 biases the L-shaped arm into engagement with the cam 222. Rotation of the lever 220 will cause the cam 222 to pivot the arm 223, causing extension and contraction of the spring 225.

A connector 230 is carried on the tubular section 201. A circumferential groove 209 is formed in the connector 230. A yoke 226 extends into the groove 209. A rod 227 interconnects the yoke 226 and the L-shaped arm 223. When the arm 223 is pivoted by the cam 222, the rod 227 pushes or pulls the yoke 226 to move the tubular shaft section 201 between its extended and retracted positions.

The connector 230 carries a groove 231 which extends diametrically of the shaft section 201. When the X-ray source 26 is oriented vertically downwardly, the groove 231 extends vertically. Referring to FIG. 3, when the shaft section 201 is extended, the connector 230 projects through an opening 233 formed in the collar 90, but does not project through an aligned opening 234 formed in the column 60. When the shaft section 201 is retracted, the connector 230 is withdrawn from the opening 233.

The positioning of the locking pin 145 is controlled by the lever 220. Referring to FIG. 3, the locking pin 145 is slidably carried by the bearing block 204. A bracket 240 is connected to the locking pin 145 and extends upwardly to a position between the collars 208, 210. A tension coil spring 241 is secured at opposite ends to the bearing block 204 and the bracket 240. The spring 241 biases the locking pin 145 toward a position of engagement with the locking block 146.

When the tubular shaft 201 is retracted, as by moving the lever 220 to the positions shown in FIGS. 3 and 10, the collar 210 engages the bracket 240 and pulls the pin 145 out of engagement with the locking block 146. When the tubular shaft 201 is extended, as shown in FIG. 4, the collar 210 disengages the bracket 240 and permits the spring 241 to move the locking pin 145 into engagement with the locking block 146.

B. The Column-carried Drive Components

Referring to FIGS. 2, 3 and 4, a hollow tubular drive shaft 250 extends vertically within the column chamber 63. A bearing block 252 is secured to the mounting plate 61 and journals the lower end of the shaft 250. A shaft extension 253 is welded to the upper end of the shaft 250. A pair of bushings 254, 255 are carried by the brackets 120, 121 and journal the shaft extension 253.

Referring to FIGS. 3 and 4, a miter gear segment 260 is carried on the shaft extension 253 at a location between the brackets 120, 121. A miter gear 261 meshes with the miter gear segment 260. A stub shaft 262 is rigidly connected to the miter gear 261. A pair of bushings 263, 264 journal the miter gear 261 and the stub shaft 262 for rotation about a horizontal axis. The bushing 263 is supported by the plate 118. A bracket 265 is welded to the bracket 121 and supports the bushing 264.

A connector 270 is carried on the stub shaft 262 adjacent the miter gear 261. As is best shown in FIG. 10, the connector 270 is provided with a tongue 271 adapted to extend into the groove 231 of the connector 230 when the connector 230 is extended through the opening 223. As will be explained, when the base carriage 40 positions the tower 23 centrally along the table top 21, the slot 231 extends vertically. When the tongue 271 of the connector 270 engages the groove 231 of the connector 230, a driving connection is established that will cause the X-ray source 26 to rotate about the axis of the hollow shaft 160 in response to rotation of the column-carried drive shaft 250.

Referring to FIG. 2, a mounting bracket 280 is secured to the lower end region of the column 60. A vertically extending pin 281 is journaled by the bracket 280. An upper arm 282 and a lower arm 283 are pivotally mounted by the pin 281 for rotation about a vertical axis indicated by the numeral 284. The lower arm 283 is a tubular duct for guiding the power cables 28 from the pedestal 22 to the lower end of the tubular conduit 24.

A pair of fan gears 285, 286 drivingly connect the upper arm 282 and the drive shaft 250. The fan gear 285 is connected to the lower end region of the drive shaft 250. The fan gear 286 is connected to the upper arm 282. The fan gears 285, 286 are identical in construction and are operative to rotate the shaft 250 in response to rotation of the upper arm 282 about the axis 284.

C. The Pedestal-carried Drive Components

Referring to FIG. 2, a mounting plate 300 is rigidly supported in the base of the pedestal 22. A pair of spaced bearing blocks 301, 302 and a reversible drive motor 303 are supported atop the mounting plate 300. A threaded rod 304 is journaled by the bearing blocks 301, 302. A ball bearing speed reducer 305 drivingly connects the motor 303 and the threaded rod 304.

Figure 9:
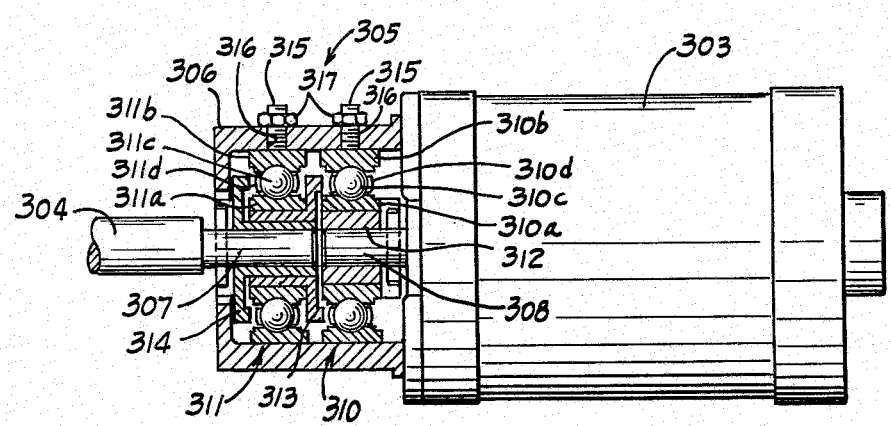
FIG. 9 is an enlarged view of a portion of the structure shown in FIG. 2 with some portions broken away to illustrate details of construction.

The ball bearing speed reducer 305 is of identical construction to the speed reducer 164 which drivingly interconnects the arm extension motor 163 and the arm extension rod 165. Referring to FIG. 9, the speed reducer 305 includes a cylindrical housing 306. The threaded rod 304 has a reduced diameter end region 307 which projects into one end of the housing 306. The motor 303 has a drive shaft 308 which projects coaxially into the opposite end of the housing 306.

A pair of ball bearings 310, 311 are carried in the housing 306. The bearings 310, 311 have inner races 310a, 311a, outer races 310b, 311b, a plurality of balls 310c, 311c interposed between the races 310a, 311a and 310b, 311b, and ball cages 310d, 311d which circumferentially space the balls 310c, 310d around the inner races 310a, 311a.

A bushing 312 is interposed between and drivingly connects the inner race 310a and the motor drive shaft 308. A sleeve 313 drivingly interconnects the cage 310d and the inner race 311a. A sleeve 314 drivingly interconnects the cage 311d and the rod end region 307.

Three pairs of set screws 315 (only one pair is shown in FIG. 9) are threaded into apertures 316 formed in the housing 306. The pairs of set screws 315 are equally spaced circumferentially of the housing 306. The inner ends of the set screws 315 engage the outer races 310b, 311b and prevent relative rotation between the outer races 310b, 311b and the housing 306. By adjusting the torque to which the set screws 315 are tightened into engagement with the outer races 310b, 311b, the preload force applied to the bearing balls 310c, 311c is controlled. Lock nuts 317 secure the set screws 315 in place once the desired torque has been applied to the set screws 315.

The speed reducer 305 is operable to effect approximately a 7 to 1 speed reduction. The inner race 310a rotates at 2½ times the speed of the cage 310d. The inner race 311a rotates at about 2½ times the speed of the cage 311d. The threaed rod 304 accordingly rotates at about one-seventh the speed of the motor drive shaft 308.

Referring to FIGS. 2 and 15, a carriage 320 is supported on the threaded rod 304. The carriage 320 includes a threaded nut 321 which is threaded onto the rod 304. A plate 319 is supported atop the nut 321. When the motor 303 rotates the threaded rod 304 in one direction, the carriage 320 moves leftwardly (as viewed in FIG. 2) along the rod 304. When the motor 303 rotates the rod 304 in the opposite direction, the carriage 320 moves rightwardly along the rod 304.

A vertically extending pivot pin 325 is journaled by the carriage 320. A sprocket 328 is secured to the lower end region of the pivot pin 325. A swivel plate 326 is mounted on the upper end region of the pin 325 for rotation together with the sprocket 328 about an axis indicated by the numeral 327.

A roller chain 328a is reeved around the sprocket 328 and around a sprocket 329. The sprocket 329 is rotatably carried by an encoder assembly 330. The encoder assembly 330 is supported on the plate 319 and operates to monitor the pivotal movement of the swivel plate 326 relative to the carriage 320 as will be explained in Section VII of this specification.

The effect of moving the carriage 320 leftwardly or rightwardly along the threaded rod 304 is to vary the distance, as measured laterally of the table top 21, between the axes 284, 327. This laterally measured distance is indicated by the reference character A in FIG. 2. While the true distance between the axes 284, 327 will vary as the column 23 moves longitudinally of the table top 21, the laterally measured component A of the true distance is solely a function of the positioning of the carriage 320 by the motor 303.

Referrring to FIG. 15, the position of the carriage 320 along the threaded rod 304 is monitored by a rotary encoder assembly 336. The encoder assembly 336 is supported on the mounting plate 300 and carries a rotatable sprocket 337. A roller chain 338 is reeved around the sprocket 337 and around a sprocket 339. The sprocket 339 is supported on the threaded rod 304 and serves to drive the encoder sprocket 337. The encoder assembly 336 monitors the position of the carriage 320 as will be described in Section VI of the specification.

A total of eight rollers are carried on the swivel plate 326. These rollers are positioned in laterally spaced pairs 331, 332, 333, 334, and only one roller from each pair appears in FIG. 2. The roller pairs 331, 332 engage opposite sides of the upper arm 282. The roller pairs 333, 334 engage opposite sides of an arm 335.

The roller pairs 331, 332 effectively establish a sliding connection between the swivel plate 326 and the upper arm 282. As the tower 23 moves longitudinally of the table top 21 in response to operation of the base carriage drive motor 55, the sliding connection between the swivel plate 326 and the upper arm will cause the swivel plate to pivot about the axis 327, and will cause the upper arm 282 to pivot about the axis 284. As the upper arm 282 pivots about the axis 284, the fan gears 285, 286 effect corresponding rotation of the drive shaft 250.

The roller pairs 333, 334 operate to rotate the arm 335 concurrently with the swivel plate 326, while permitting relative sliding movement between the arm 335 and the swivel plate 326. The roller pairs 331, 332, 333, 334 are arranged such that the paths of permitted relative sliding movement between the arms 335, 282 and the swivel plate 326 are parallel and intersect the axes 327, 284.

A linear cam member 340 is supported by the pedestal 22. The cam member 340 extends longitudinally of the table top 21 and defines a downwardly opening, longitudinally extending recess 341. A pin 342 is carried on the forward end region of the arm 335 and extends into the recess 341. The pin 342 has an axis indicated generally by the numeral 343. The pin 342 and the recess 341 establish a sliding, pin-in-slot connection which maintains the axis 343 laterally fixed relative to the table top 21 as the arms 335, 282 rotate during movement of the tower 23 longitudinally of the table top 21.

D. The Bucky tray Drive System

The movement of the pin 342 longitudinally of the table top 21 is utilized to drive the Bucky tray 30 longitudinally of the table top 21 during tomographic procedures. As will be explained in greater detail, the lateral distance between the axes 343, 327 determines the distance through which the Bucky tray 30 will be moved longitudinally of the table top 21 in response to movement of the tower 23 through a given longitudinal distance.

The lateral distance between the axes 343, 327 is indicated in FIG. 2 by the reference character B. As the distance B increases, the distance longitudinal of the table top through which the pin 342 is caused to move (as the tower 23 moves a given distance) will increase. As the distance B decreases, the distance longitudinal of the table top through which the pin 342 is caused to move (as the tower 23 moves a given distance) will decrease.

The mechanism which transmits motion from the pin 342 to the Bucky tray 30 includes a welded, U-shaped arm 350. The arm 350 has parallel, overlying upper and lower portions 351, 352 which are interconnected by a cylindrical central stem portion 353.

A pair of vertically spaced bearing blocks 355 are mounted on the mounting plate 51. The stem portion 353 of the U-shaped arm 350 has end regions 356 which are journaled by the bearing blocks 355. The bearing blocks 355 pivotally support the arm 350 for movement about the axis of the stem portion 353.

A sliding bearing 360 is carried on the distal end of the lower arm portion 352. A slide 361 is slidably carried in the bearing for movement longitudinal of the lower arm portion 352. The slide 361 is pivotally connected to the pin 342. As the pin 342 reciprocates longitudinally of the table top 21, the connection between the slide 361 and the lower arm portion 352 causes the arm 350 to pivot about the axis of the stem portion 353.

A Bucky tray drive bar 365 is positioned above the upper arm portion 351. The bar 365 is pivotally carried on the upper stem end region 356 and is pivotal about the axis of the stem portion 353 independent of the movement of the U-shaped arm 350.

The Bucky tray 30 is supported in a carriage 366. The carriage 366 is supported on bearings, not shown, and is constrained such that it can only move longitudinally of the table top 21. A pin 367 depends from the carriage 366 and extends into a slot 368 formed in the Bucky tray drive bar 365. The axis of the pin 367 is coaxial with the axis 343 of the pin 342. When the Bucky tray drive arm 350 pivots about the axis of the stem portion 353 in response to movement of the pin 342, the movement of the pin 342 is transmitted to the pin 367 causing the Bucky tray 30 to move longitudinally of the table top 21.

A solenoid operated latch, indicated generally by the numeral 370, is carried on the upper arm portion 351 and is operable to selectively connect and disconnect the upper arm portion 351 and the drive bar 365. When the upper arm portion 351 and the drive bar 365 are connected by the latch 370, they pivot together about the axis of the stem portion 353 in response to longitudinal movement of the tower 23 along the table top 21. When the upper arm portion 351 and the drive bar 365 are disconnected by the latch 370, longitudinal movement of the tower 23 will have no driving effect on the Bucky drive bar 365.

Figure 11:
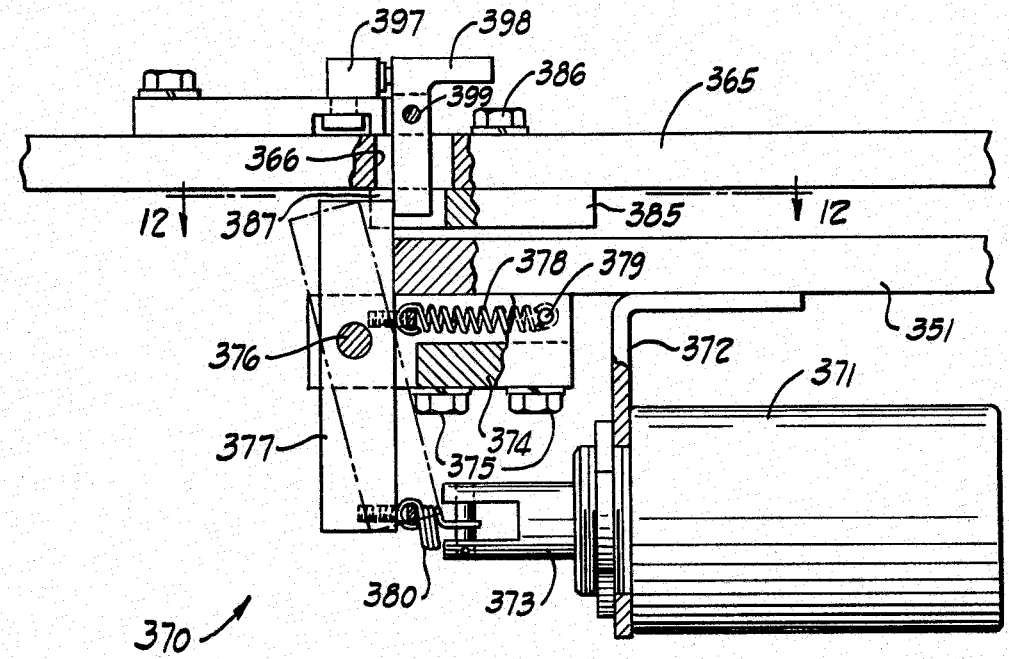
FIG. 11 is an enlarged view of a portion of the structure shown in FIG. 2 with some portions broken away to illustrate details of construction.

Referring to FIG. 11, the solenoid operated latch 370 includes a solenoid 371. A bracket 372 mounts the solenoid 371 on the upper arm portion 351. The solenoid 371 has an armature 373 which is normally extended to the position shown in FIG. 11. When the solenoid 371 is electrically energized, it moves the armature 373 rightwardly, as viewed in FIG. 11.

A mounting block 374 is supported on the upper arm portion 351 at a position above the armature 373. Threaded fasteners 375 secure the mounting block 374 to the arm portion 351. A pin 376 is carried by the mounting block 374. A latch pawl 377 is pivotally supported on the pin 376. A tension coil spring 378 is connected at one end to the pawl 377 and at its other end to a pin 379 supported in the mounting block 374. The spring 378 biases the pawl 377 clockwise, as viewed in FIG. 11 toward a position where the pawl 377 abuts the end of the arm portion 351.

A tension coil spring 380 interconnects the pawl 377 and the armature 373. When the solenoid 371 is energized to move the armature 373 rightwardly, as viewed in FIG. 11, the spring 380 is operative to pivot the pawl 377 counterclockwise to the position shown in phantom in FIG. 11.

Figure 12:
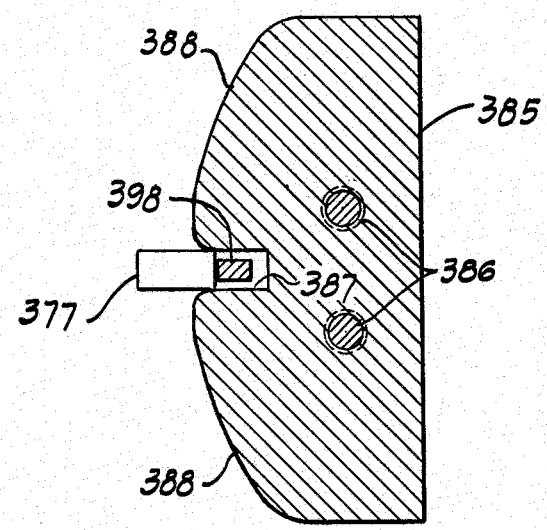
FIG. 12 is a sectional view as seen from a plane indicated by a line 12—12 in FIG. 11.

Referring to FIGS. 11 and 12, a latching block 385 is supported on the Bucky drive bar 365 by threaded fasteners 386. A forwardly facing notch 387 is formed in the latching block 385. When the pawl 377 is received in the notch 387, as when the solenoid 371 is de-energized, the Bucky tray drive bar 365 and the upper arm portion 351 are latched together. When the pawl 377 is pivoted to the position shown in phantom in FIG. 11, as when the solenoid 371 is energized, the pawl 377 is not received in the notch 387, and relative movement is permitted between the upper arm portion 351 and the Bucky tray drive bar 365.

Positioning the pawl 377 in the notch 387 is facilitated by inclined surfaces 388 formed on the mounting block 385 on opposite sides of the notch 387. When the solenoid 377 is de-energized, movement of the Bucky drive bar 365 toward a position overlying the upper arm portion 351 will bring the pawl 377 into engagement with one of the surfaces 388. As the Bucky tray drive bar continues to move toward a position overlying the upper arm portion 351, the surface 388 engaged by the pawl 377 will pivot the pawl 377 in opposition to the action of the spring 378. As the drive bar 365 reaches a position overlying the upper arm portion 351, the pawl 377 will pivot into the notch 387, locking the drive bar 365 to the upper arm portion 351.

E. Position Sensors and Safety Interlocks

Before a tomograph can be made with the X-ray apparatus 20, several conditions must be met:
1. The tube rotation detent assembly 179 must be unlatched to permit rotation of the X-ray source 26 about the axis of the shaft 160;
2. The extensible arm 25 must be properly retracted to position the X-ray source 26 in a centered position above the Bucky tray 30;
3. The arm 25 must be positioned forwardly to extend over the table top 21;
4. The carriage 24 must be positioned at the proper height above the table top to permit connection between the connectors 230, 270;
5. The connectors 230, 270 must be connected to transmit rotation from the vertical drive shaft 250 to the horizontal drive shaft 200;
6. The Bucky tray drive arm 365 must be connected by the pawl 377 to the upper arm portion 351; and,
7. The base carriage 40 must be properly positioned longitudinally of the table top 21.

Sensors are preferably provided for sensing compliance with all of these conditions.

Referring to FIG. 7, a limit switch 390 is carried within the mounting block 161 to sense when the detent projection 188 is engaging one of the notches 180, 181, 182. The switch 390 is positioned to be engaged by the arm 190 when the detent projection 188 is engaging one of the notches 180, 181, 182, and to be disengaged by the arm 190 when the detent projection 188 is out of the notches 180, 181, 182. By this arrangement, the switch 390 provides a variation in an electrical signal indicative of when the tube detent assembly 179 has unlatched to permit rotation of the X-ray source about the axis of the shaft 160.

Referring to FIG. 3, a limit switch 391 is carried within the housing 143. An inclined cam surface 392 is provided atop the tubular member 151. The switch 391 is positioned to be engaged by the cam 392 and provides a variation in an electrical signal indicative of when the extensible arm 25 is properly retracted to a centered position for tomographic operation.

Referring again to FIG. 3, a limit switch 393 is carried within the housing 143. The switch 393 is positioned to be engaged by the collar 210 when the extensible tubular shaft section 201 has extended, and to be disengaged by the collar 210 when the shaft section 201 is retracted. By this arrangement, the switch 393 provides a variation in an electrical signal indicative of when the arm 25 is locked in a forward position.

Referring to FIG. 2, a pair of limit switches 394, 395 are carried within the column 60. The switches 394, 395 are positioned to be engaged by the nut 123 as the nut moves along the threaded rod 124. The switch 394 is positioned above the switch 395 and is operative to provide a variation in an electrical signal when the carriage 24 is positioned two inches below the location where the connector 230 makes driving connection with the connector 270 when the tubular shaft section 201 is extended. The switch 395 provides a variation in an electrical signal in response to positioning of the carriage 24 at the proper height where driving connection is established between the connectors 230, 270.

Referring again to FIG. 2, a switch 396 is carried by the mounting plate 51. The switch 396 is positioned to be engaged by the base carriage 40 when the base carriage 40 has positioned the tower 23 at a centered position longitudinally of the table top 21, and to be disengaged by the base carriage 40 when the base carriage 40 is in an uncentered position. The switch 396 provides a variation in an electrical signal indicative of when the base carriage 40 is in a centered position.

Referring to FIG. 11, a limit switch 397 is carried atop the Bucky tray drive bar 365. An actuating lever 398 is pivotally mounted by a pin 399 and depends through an aperture 366 formed in the bar 365. When the pawl 377 is received in the slot 387, the pawl 377 engages the lever 398, pivoting the lever 398 into engagement with the switch 397. When the pawl 377 is removed from the slot 387, the lever 398 pivots under the influence of gravity to a position where it disengages the switch 377. The switch 397 is accordingly operative to provide a variation in an electrical signal indicative of when the Bucky drive bar 365 is drivingly coupled to the upper arm portion 351.

In the preferred practice of the invention, the sensing switches 390, 391, 393, 394, 395, 396 and 397 are connected in safety interlock control circuits which will:

1. When radiographic operation has been selected, retain the carriage 24 at a position below that where driving connection is established between the connectors 230, 270, as sensed by the switch 394, whereby no driving connection is established between the connectors 230, 270 during radiography.

2. Prevent the motor 126 from elevating the carriage 24 to a position where connection is made between the connectors 230, 270 unless:
   a. The tower 23 is centered longitudinally of the table top 21, as indicated by the switch 396;
   b. The tube rotation detent assembly 179 has been unlatched, as indicated by the switch 390;
   c. The extensible arm 25 has been properly retracted for tomographic operation, as indicated by the switch 391; and,
   d. The arm 25 is properly latched forwardly of the column 23, as indicated by the switch 393.

3. Prevent the movement of the base carriage 40 from a centered position longitudinally of the table top 21 rightwardly to a "tomograph ready" position as by operation of the motor 55 unless:
   a. The carriage 24 has been elevated to a position where connection has been made between the connectors 230, 270, as indicated by the switch 395; and,
   b. The Bucky tray drive bar 365 is drivingly connected to the upper arm portion 351, as indicated by the switch 397.

Since circuitry for effecting such safety interconnection of the switches 390, 391, 393, 394, 395, 396, 397 and the motors 55, 126 is conventional and forms no part of the present invention, it need not be described.

F. Operation of the Tomographic Drive System

Figure 13:
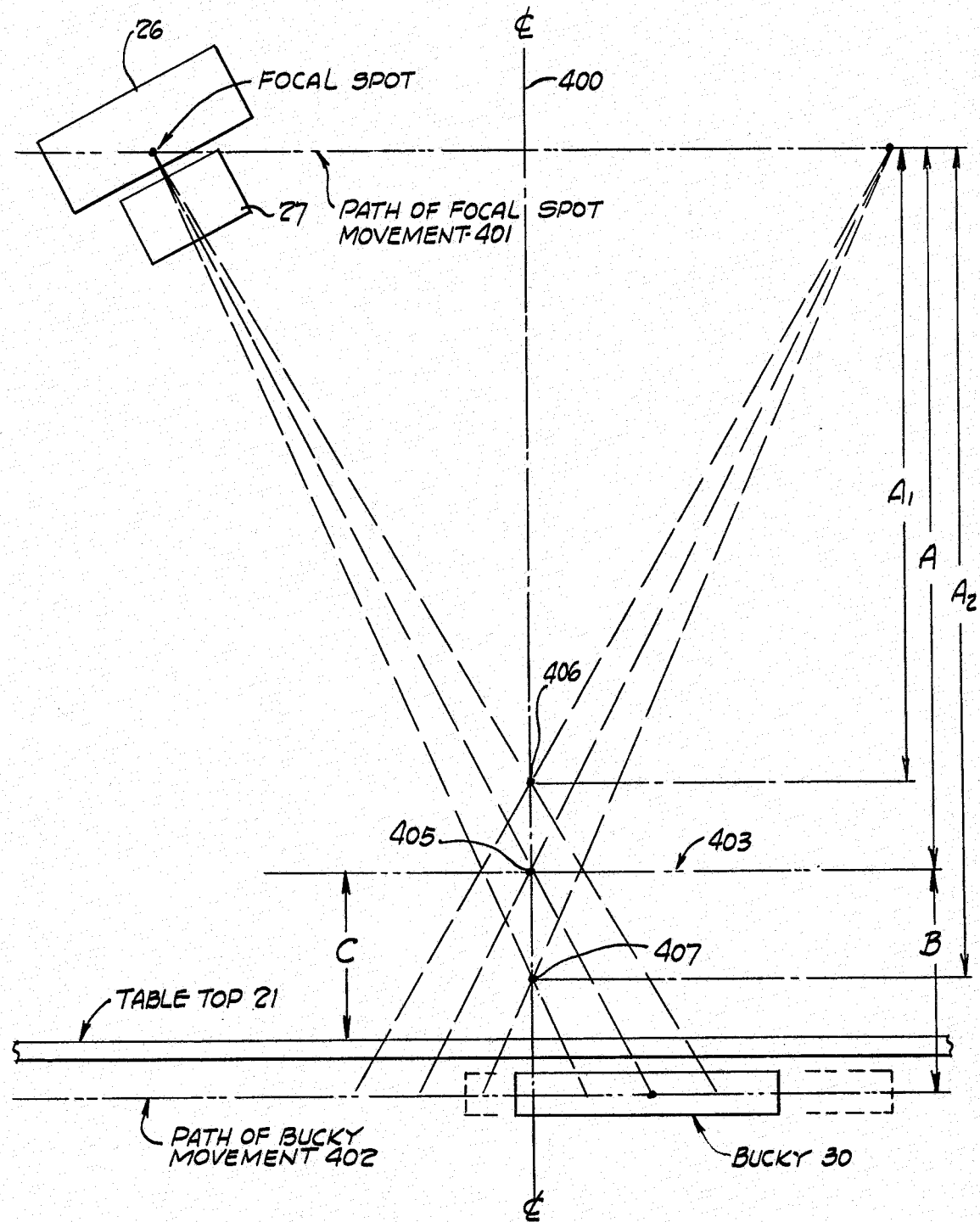
FIG. 13 is a schematic front elevational view of portions of the apparatus shown in FIG. 1.
Figure 14:
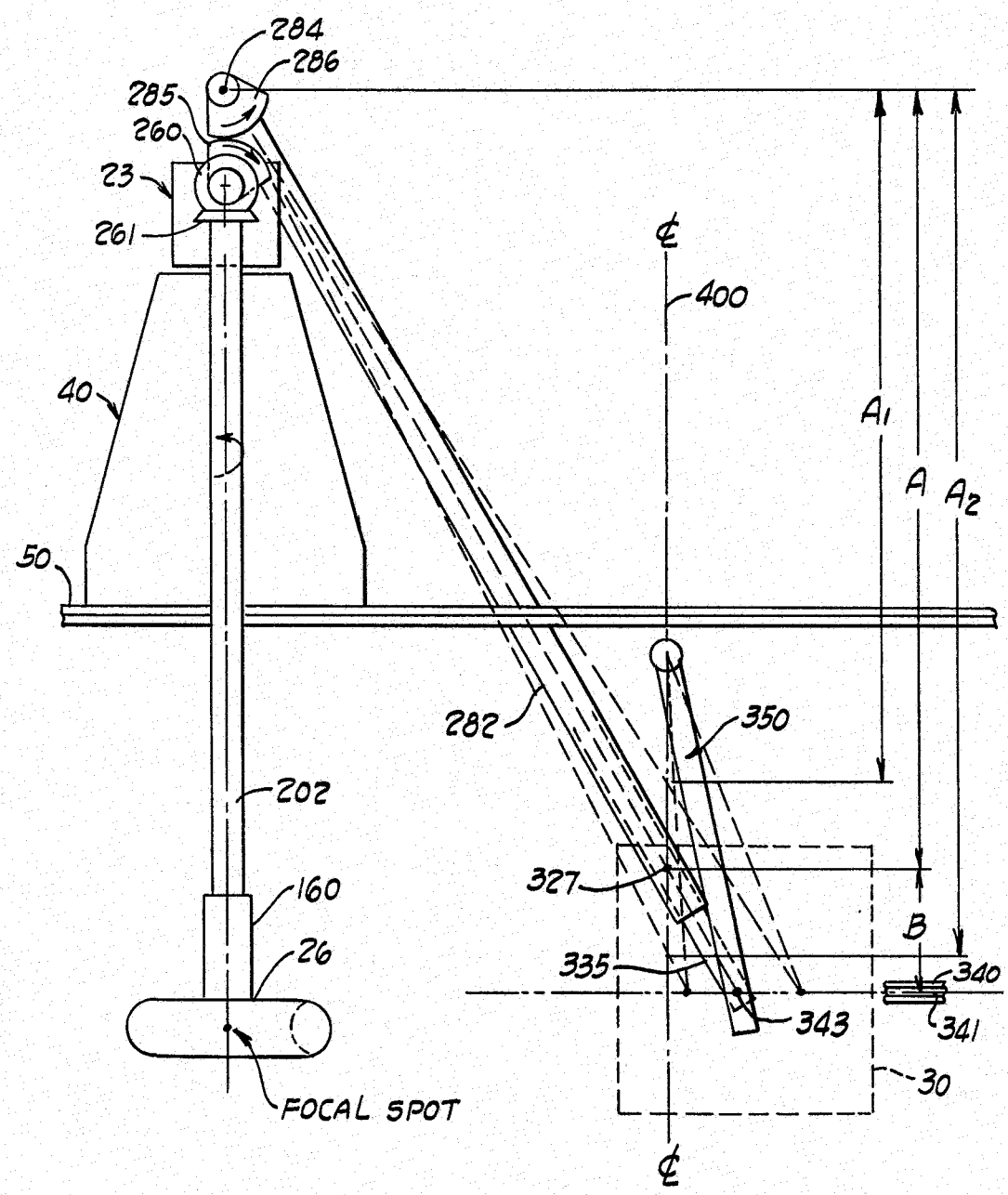
FIG. 14 is a schematic top plan view of portions of the apparatus shown in FIG. 1.

In order to facilitate an understanding of the operation of the tomographic drive system, schematic illustrations of certain of the components of the X-ray apparatus 20 are shown in FIGS. 13 and 14. FIG. 13 is a side elevational schematic view showing the table top 21, the X-ray source 26 positioned above the table top 21, and the Bucky tray 30 positioned beneath the table top 21. FIG. 14 is a top plan schematic view showing the base carriage 40, the track 50 along which the base carriage 40 moves, the tower 23 supported on the base carriage 40 and the X-ray source 26. Also shown in FIG. 14 are several of the drive system components which interconnect the Bucky tray 30 and the X-ray source 26.

Referring to FIGS. 13 and 14, the numeral 400 designates what will be called a "center plane." The center plane 400 is a vertical plane which extends laterally of the table top 21. The axis of the threaded rod 304 (FIG. 2) is located within the plane 400.

When a tomograph is to be made, a patient is positioned on the table top 21 with the patient's center of interest intersected by the center plane 400. The X-ray source 26 and the Bucky tray 30 are then driven back and forth respectively above and below the patient's center of interest to produce a shadow image of portions of the patient's anatomy which lie in in examination plane extending through the patient's center of interest. One such examination plane is indicated by the numeral 403 in FIG. 13.

Referring to FIG. 13, the path of movement of the X-ray source 26 during tomography is indicated by the numeral 401. The path of movement of the Bucky tray 30 during tomography is indicated in FIG. 13 by the numeral 402.

The vertical distance between the paths 401, 402 is the sum of two distances "A" and "B." The distance "A," as depicted in FIG. 13, is the vertical distance from the path 401 to the examination plane 403. The distance "B," as depicted in FIG. 13, is the vertical distance from the path 402 to the examination plane 403. While the distances "A" and "B" are adjustable to raise or lower the examination plane 403, the sum of two distances "A" and "B" is fixed.

The distances "A" and "B" as depicted in FIG. 13 are exactly the same distances as are indicated by the characters "A" and "B" in FIGS. 2 and 14. In FIGS. 2 and 14, the distance "A" is the distance (measured laterally of the table top 21) between the axes 284, 327, and the distance "B" is the distance (measured laterally of the table top 21) between the axes 327, 343.

The distances "A" and "B" can be adjusted by energizing the motor 303 to move the carriage 320 along the threaded rod 304. As the carriage 320 moves along the threaed rod 304, it changes the distance between the axis 327 and the axes 284, 343. When the carriage 320 positions the axis 327 at the location shown in FIG. 2, the central axis of the beam of X-rays emitted from the source 26 will cross the center plane 400 at a point 405 (FIG. 13) within the examination plane 403 as the source 26 moves back and forth along the path 401.

The position of the examination plane 403 is specified by a distance "C" shown in FIG. 13. The distance "C" is the distance from the table top 21 to the examination plane 403. As will be explained, the rotary encoder assembly 336 forms part of a system which provides a digital readout in millimeters of the position of the examination plane 403. A "zero" reading indicates that the examination plane 403 is coincident with the table top 21.

The location of a tomographic examination plane 403, i.e., the height of the examination plane 403 above the table top 21, is determined by the ratio of "A" to "B." If the distance "A" is diminished to a distance "A1," as by operating the drive motor 303 to move the carriage 320 rearwardly (rightwardly as viewed in FIG. 2) along the threaded rod 320, the effect will be to cause the arm 282 to pivot through a greater arc about the axis 284 as the tower 23 moves longitudinally of the table top 21 a given distance. The increased arcuate movement of the arm 282 will be transmitted to the X-ray source 26 through the drive components which interconnect the source 26 and the arm 282, causing the souce 26 to rotate through a greater arc about the axis of the shaft 160 as the tower 23 moves longitudinally of the table top 21 a given distance. Rotation of the source 26 through an increased arc will cause the central axis of the beam of X-rays emitted from the source 26 to cross the center plane 400 at a point 406 above the point 405, thereby establishing an examination plane above the plane 403.

If the distance "A" is increased to a distance "A2," as by operating the drive motor 303 to move the carriage 320 forwarly (leftwardly as viewed in FIG. 2) along the threaded rod 320, the effect will be to cause the arm 282 to pivot through a lesser arc about the axis 284 as the tower 23 moves longitudinally of the table top 21 a given distance. The decreased arcuate movement of the arm 282 will be transmitted to the X-ray source 26 through the drive components which interconnect the source 26 and the arm 282, causing the source 26 to rotate through a lesser arc about the axis of the shaft 160 as the tower 23 moves longitudinally of the table top 21 a given distance. Rotation of the source 26 through a decreased arc will cause the central axis of the beam of X-rays emitted from the source 26 to cross the center plane 400 at a point 407 below the point 405, thereby establishing an examination plane below the plane 403.

Regardless of the "A to B" ration which may be selected, the drive components which interconnect the arm 282 and the Bucky 30 will operate to keep the center of the Bucky tray 30 aligned with the center of the X-ray beam emitted from the source 26. The ratio of the distances through which the source 26 and the Bucky tray 30 move relative to the center plane 400 is exactly the ratio "A to B." Hence, if the distance "A" is decreased to raise the examination plane 403, whereby the distance "B" is correspondingly increased, the travel of the Bucky tray 30 along the path 402 will be increased to keep the center of the Bucky tray 30 aligned with the center axis of the X-ray beam emitted from the source 26. Similarly, if the distance "A" is increased to lower the plane of cut 403, whereby the distance "B" is correspondingly decreased, the travel of the Bucky tray 30 along the path 402 will be decreased to keep the center of the Bucky tray 30 aligned with the center axis of the X-ray beam emitted from the source 26.

Referring to FIG. 2, such an increase or decrease in Bucky tray travel results because the linear cam 340 constrains the pin 342 to move longitudinally of the table top 21. The greater the distance "B," the greater will be the distance traversed by the pin 342 as the tower 23 moves longitudinally of the table top 21 a given distance. As has been explained, the movement of the pin 342 is transmitted to the Bucky tray 30 and in fact represents the exact movement executed by the Bucky tray 30 during tomography.

VII. Indication of the Plane of Tomographic Examination by the Encoder Assembly 336

Referring to FIG. 16 the rotary encoder assembly 336 includes a generally cylindrical housing 451. A pair of end plates 452, 453 close opposite ends of the housing 451. A pair of bearings 454, 455 are carried by the end plates 452, 453. A shaft 456 is journaled by the bearings 454, 455. A disc 457 is carried on the shaft 456 at a location inside the housing 451. A sensor unit 460 is secured to the housing 451. The sensor unit 460 includes a light source 461 and a photocell 462. The light source 461 and the photocell 462 are positioned on opposite sides of the disc 457.

Referring to FIG. 17, three equally spaced slots 463 are formed in peripheral portions of the disc 457. When one of the slots 463 aligns with the light source 461 and the photocell 462, light from the source 461 is received by the photocell 462. When none of the slots 463 align with the source 461 and the photocell 462, the disc 457 blocks transmission of light from the source 461 to the photocell. By this arrangement, the photocell 462 provides an intermittent electrical signal with pulses which indicate the passage of light through one of the slots 463. Since the disc 457 carries three of the slots 463, each revolution of the disc 457 will provide three pulses in the signal from the photocell 462.

The threaded rod 304 has a pitch of three millimeters, which means that each revolution of the rod 304 is operative to move the carriage 320 through a distance of 3 millimeters. Since the encoder assembly 336 provides three signal pulses per revolution, each signal pulse indicates a one millimeter movement of the carriage 320.

The output signal from the photocell 462 is fed to a digital readout system, indicated generally by the numeral 470 in FIG. 16. The readout system 470 is of conventional construction and includes a digital readout scale 471. The scale 471 provides a readout in millimeters within the range of 0–250 mm. of the distance "C," i.e., the height of a tomographic examination plane above the table top 21. Each pulse from the photocell 462 is counted by the system 470 and serves to increase or decrease the digital reading on the scale 471 by one millimeter depending on whether the examination plane 403 is being raised or lowered relative to the table top 21. Other circuitry, not shown, connects with system 470 to inform the system about the direction of rotation of the drive motor 303 so that the system 470 will know whether the examination plane 403 is being raised or lowered as the motor 303 operates.

VIII. Control of Source Operation During Tomography by the Encoder Assembly 330

The encoder assembly 330 is identical in construction to the encoder assembly 336 except for the arrangement of signaling slots formed in its shaft-carried disc. Referring to FIG. 18, the disc used in the encoder assembly 330 is indicated generally by the numeral 480. A total of eight slots, 481, 482, 483, 484, 485, 486, 487, 488 are formed in peripheral portions of the disc 480. The slots 481–484 and 485–488 are arranged symmetrically about an imaginary line 490 which extends radially of the disc 480.

The slots 484, 485 are located 12½° around the disc 480 on opposite sides of the line 490, which gives a 25° spacing between the slots 484, 485. The slots 483, 486 are located 25° around the disc 480 on opposite sides of the line 490 which gives a 50° spacing between the slots 483, 486. The slots 482, 487 are located 50° around the disc 480 on opposite sides of the line 490, which gives a 100° spacing between the slots 482, 487. The slots 481, 488 are located 100° around the disc 480 on opposite sides of the line 490, which gives a 200° spacing between the slots 481, 488.

The disc 480 is mounted on the shaft of the rotary encoder assembly 330 such that, when the X-ray source 26 and the Bucky tray 30 are located in the center plane 400, the imaginary line 490 is aligned with the light source and the photocell of the encoder assembly 330. Movement of the source 26 leftwardly or rightwardly of the center plane 400 will cause corresponding counterclockwise or clockwise rotation of the disc 480 relative to the source and photocell of the encoder assembly 330.

The ratio of the sizes of the sprockets 328, 329 (FIG. 15) is selected such that the encoder disc 480 rotates through five times the amount of rotation of the swivel plate 326 relative to the carriage 320. Since rotation of the swivel plate 326 accurately eflects rotation of th source 26 about the imaginary pivot axis 405, the encoder disc 480 rotates through five times the arc of rotation of the source 26.

If the source 26 pivots back and forth through an arc which extends only 2½° to either side of the center plane 400, the encoder disc will move through a total rotation of 25° between positions where the slots 484, 485 are selectively aligned with the source and photocell of the encoder assembly 300. The signals provided by the photocell of the encoder assembly 330 when the slots 484, 485 transmit light to the encoder photocell can be used to start and stop the source 26 so that the source is active through only a 5° range of movement. A tomography procedure of this type is called "zonography" and is used where a thick examination plane of cut is desired and where only peripheral details are desirably blurred in the resulting image.

Signals provided by the photocell of the encoder assembly 330 when others of the slots 481–488 transmit light to the encoder photocell can be used to start and stop the source 26 so that the source is active through such ranges of movement as 10°, 20° and 40°. The larger is the range of active source movement, the thinner is the resulting examination plane of cut. A 40° range of active source movement will, for example, leave a clear image of anatomical portions which lie within about a 1-millimeter thick examination plane of cut.

Suitable electronic circuitry of conventional design connects with the encoder assembly 330 and with the source 26 such that:

1. If a 5° exposure angle is desired, as for zonography, the source 26 is energized between the fourth and fifth pulses of the encoder 330 which result from an alignment of the disc slots 484, 485 with the encoder light source and photocell;
2. If a 10° exposure angle is desired, the source 26 is energized between the third and sixth encoder pulses, which correspond to the disc slots 483, 486;
3. If a 20° exposure angle is desired, the source 26 is energized between the second and seventh encoder pulses, which correspond to the disc slots 482, 487; and,
4. If a 40° exposure angle is desired, the source 26 is energized between the first and eighth encoder pulses, which correspond to the disc slots 481, 488.

IX. Operation of the Apparatus 20 During Raiography

The apparatus 20 is easily converted from tomographic to radiographic operation simply by:

1. lowering the carriage 24 to disconnect the connectors 230, 270; and,
2. Energizing the solenoid 371 (FIG. 1) to disconnect the Bucky tray drive bar 365 from the upper arm portion 351.

Once these simple steps are complete, the source 26 and the Bucky tray 30 may be moved independently relative to each other and relative to the table top 21 for the taking of conventional radiographs.

Converting the apparatus 20 from radiographic operation to tomographic operation is accomplished by:

1. De-energizing the solenoid 371 and moving the Bucky tray 30 to a centered position along the table top 21 where the pawl 377 pivots into the slot 387 to lock the Bucky drive bar 365 to the upper arm portion 351;
2. Raising the carriage 24 to connect the connectors 230, 270; and,
3. Moving the tower 23 rightwardly to a position of readiness for initiating the production of a tomograph.

Although the invention has been described in its preferred form with a certain degree of particularly, it is undertood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. An X-ray apparatus operable selectively and one at a time for radiography and tomography, comprising:
   a. an X-ray source device providing a beam of X-radiation;
   b. an X-ray imaging device responsive to incident X-radiation;
   c. a patient support for positioning portions of a patient between said devices;
   d. structure extending between and mounting said devices for independent movement relative to each other and relative to the support;
   e. drive means for selectively interconnecting and driving said devices through coordinated movements for tomography; and,
   f. the drive means being housed within and shielded by the structure and including means for automatic interconnection.

2. The apparatus of claim 1 wherein one of said devices is movable relative to said structure and said drive means includes components which are connected and disconnected in driving relationship when said one device is positioned in and out of a predetermined location relative to said structure.

3. The apparatus of claim 2 additionally including sensor means for sensing when said one device is in and out of said predetermined location.

4. The apparatus of claim 1 wherein said drive means includes electrically operated latch means for selectively interrupting and establishing an interconnection between said drive means and one of said devices.

5. The apparatus of claim 4 additionally including sensor means for sensing when such interconnection is interrupted and established.

6. The apparatus of claim 1 including a separate electrically operated means associated with each of said devices for selectively interrupting and establishing driving connection between its associated device and components of said drive means.

7. The apparatus of claim 6 additionally including separate sensor means for sensing when each of such driving connections are interrupted and established.

8. The apparatus of claim 1 wherein:
   a. said structure includes a column which extends past said support toward said devices;

b. said structure additionally includes a carriage movable along said column;
c. one of said devices is supported by said carriage;
d. said drive system includes connectable drive components carried in said column and in said carriage;
e. said connectable drive components being connected when said carriage is in a predetermined position along said column and being disconnected when said carriage is moved out of said predetermined position.

9. The apparatus of claim 8 additionally including sensor means for sensing when said carriage is in and out of said predetermined position.

10. The apparatus of claim 8 wherein said connectable drive components are connected for rotation about a common axis when said carriage is in said predetermined position.

11. The apparatus of claim 10 additionally including sensor means for sensing when said connectable drive components are connected and disconnected.

12. An X-ray apparatus operable selectively for radiography and tomography, comprising:
 a. an X-ray device providing a source of X-radiation and an X-ray imaging device responsive to incident X-radiation;
 b. a patient support for positioning a patient between said devices;
 c. structure extending between and mounting said devices for movement relative to each other and relative to the support;
 d. one of said devices being movable relative to said structure into and out of a predetermined position;
 e. drive means operable when said one device is in said predetermined position to automatically interconnect and drive said devices through coordinated movements for tomography, and operable when said one device is one of said predetermined position to permit independent movement of said devices.

13. The apparatus of claim 12 additionally including sensor means for sensing when said one device is in and out of said predetermined position.

14. The apparatus of claim 12 wherein said drive means includes drive components which engage to establish a driving connection as said one device is moved into said predetermined position, and which disengage as said one device is moved out of said predetermined position.

15. The apparatus of claim 14 additionally including sensor means for sensing when said drive components are connected and disconnected.

16. The apparatus of claim 14 wherein said components are connected for rotation about a common axis when said one device is in said predetermined position.

17. The apparatus of claim 16 additionally including sensor means for sensing when said components are positioned for rotation about said common axis.

18. In an X-ray apparatus operable selectively and one at a time for radiography or tomography:
 a. an X-ray source device for providing a beam of X-radiation;
 b. an X-ray imaging device responsive to incident X-radiation from the X-ray generating device;
 c. a patient support disposed intermediate the X-ray source device and the X-ray imaging device for positioning portions of a patient between the devices;
 d. a mounting structure for each device, the mounting structures defining a volume;
 e. a drive mechanism for moving one of the devices, the drive mechanism being disposed within the volume; and
 f. selectively operable connecting means disposed within the mounting structures and intermediate the devices to automatically connect the devices for coordinated tomographic movements upon the driving of one of the devices.

19. The apparatus of claim 18 wherein the connecting means include mating components which may be engaged in driving relationship when the devices are located in a predetermined position with respect to the patient support.

20. The apparatus of claim 19, further comprising sensor means disposed within the mounting structures for sensing when the devices are in the proper position for engagement of the connecting means.

21. The apparatus of claim 18, further comprising electrically operated latch means for selectively interrupting and establishing a driving connection between the drive mechanism and one of the devices.

22. The apparatus of claim 21, further comprising sensor means disposed adjacent the latch means for sensing when the driving connection is interrupted and established.

23. The apparatus of claim 18, wherein the selectively operable connecting means are actuated electrically.

24. The apparatus of claim 23, further comprising a sensor means disposed adjacent each connecting means for sensing when each of the driving connections is interrupted and established.

25. An X-ray apparatus operable for radiography or tomography, comprising:
 a. a base;
 b. a generally horizontally disposed patient support carried by the base;
 c. a generally vertically disposed tower carried by the base for movement longitudinally of the patient support;
 d. a carrier supported on the tower for vertical movement longitudinally of the tower;
 e. a support arm carried by the carriage extending generally at a right angle to the tower to be supported over the patient support;
 f. an X-ray souce for providing a beam of X-radiation, the X-ray source being carried by the support arm;
 g. an X-ray imaging device responsive to incident X-radiation, the X-ray imaging device being disposed within the base and beneath the patient support so that portions of a patient may be positioned intermediate the X-ray source and the X-ray imaging device;
 h. a drive mechanism for moving the tower longitudinally of the patient support, the drive mechanism being disposed within a portion of the base and the tower so as to be shielded from patient contact; and
 i. selectively operable connecting means shielded from patient contact, the connecting means being disposed intermediate the devices for coordinated tomographic movement upon the driving of the tower.

26. The apparatus of claim 25, further comprisingg an angulating mechanism for moving the X-ray source about a longitudinal axis of the support arm.

27. The apparatus of claim 26, wherein the selectively operable connecting means comprises:

a. a first connector disposed intermediate the X-ray source and the angulating mechanism; and
b. a second connector disposed intermediate the X-ray imaging device and the drive mechanism.

28. The apparatus of claim 25, wherein the connecting means disposed intermediate the X-ray source and the drive mechanism is engageable only when the carriage is positioned in a predetermined location along the longitudinal axis of the tower.

29. The apparatus of claim 28, further comprising sensor means for sensing when the carriage is in the predetermined position.

30. The apparatus of claim 29, futher including sensor means for sensing when the connecting means disposed intermedite the X-ray source and its associated drive mechanism is engaged 31. The apparatus of claim 25, wherein the connecting means disposed intermediate the imaging device and the drive mechanism is engageable only when the imaging device is positioned in a predetermined position along the length of the base.

32. The apparatus of claim 31, further comprising sensor means for sensing when the imaging device is in the predetermined position.

33. The apparatus of claim 32, further including sensor means for sensing when the connecting means disposed intermediate the imaging device and the drive mechanism is engaged.

34. An X-ray apparatus operable for radiography or tomography, comprising:
a. a table frame and body structure including a patient support;
b. a longitudinally movable tower carried by the structure
c. a carriage movably supported on the tower for movement toward and away from the patient support;
d. an X-ray source device for providing a beam of X-radiation;
e. a source support carried by the carriage and supporting the source device over the patient support;
f. an X-ray imaging device responsive to incident X-radiation, the X-ray imaging device being disposed within the body structure and beneath the patient support so that portions of a patient may be positioned intermediate the source device and imaging device;
g. a drive mechanism for moving the tower longitudinally relative to the patient support, the drive mechanism being disposed within the body structure and shielded from patient contact;
h. selectively operable connecting means shielded from patient contact, the connecting means being disposed intermediate the devices for coordinated tomographic movement upon the driving of the tower;
i. an angulating mechanism for moving the X-ray source device about an axis;
j. the selectively operable connecting means comprising a first connector disposed intermediate the X-ray source device and the angulating mechanism, and a second connector disposed intermediate the X-ray imaging device and the drive mechanism; and
k. the first connector including matable components which can be automatically engaged only when the X-ray source device is in a predetermined position and the second connector including matable components which can be automatically engaged only when the X-ray imaging device is in another predetermined position.

35. The apparatus of claim 34, further comprising sensor means for sensing when the devices are in their respective predetermined positions with respect to the patient support.

* * * * *

UNITED STATES PATENT AND TRADEMARK OFFICE
CERTIFICATE OF CORRECTION

PATENT NO. : 4,082,955
DATED : April 4, 1978
INVENTOR(S) : Leslie James Sell

It is certified that error appears in the above-identified patent and that said Letters Patent are hereby corrected as shown below:

Column 3, line 58, after "extensible" insert -- arm --; line 67, change "the" first occurrence to -- and --.
Column 4, line 14, change "is" to -- its --; line 41, change "pir" to -- pair --.
Column 6, line 21, change "alonged" to -- aligned --; line 49, change "now" to -- not --; line 64, change "63" to -- 61 --.
Column 9, line 27, change "in" to -- is --.
Column 12, line 3, change "223" to -- 233 --; line 6, change "slot" to -- groove --.
Column 13, line 7, change "threaed" to -- threaded --.
Column 15, line 58, after "Bucky" insert -- tray --.
Column 16, line 34, delete "tube".
Column 18, line 14, change "in" second occurrence to -- an --.
Column 19, line 28, change "ration" to -- ratio --.
Column 21, line 11, change "th" to -- the --; line 59, change "Raiography" to -- Radiography --.
Column 22, line 16, change "particularly" to -- particularity --.
Column 24, line 42, change "carrier" to -- carriage --; line 64, change "comprisingg" to -- comprising --.
Column 25, line 16, change "intermedite" to -- intermediate --.

Signed and Sealed this

Twelfth Day of September 1978

[SEAL]

Attest:

RUTH C. MASON
Attesting Officer

DONALD W. BANNER
Commissioner of Patents and Trademarks